(12) United States Patent
Yao et al.

(10) Patent No.: US 9,078,942 B2
(45) Date of Patent: Jul. 14, 2015

(54) TITANIUM DIOXIDE, SINGLE-WALLED CARBON NANOTUBE COMPOSITES

(75) Inventors: Yuan Yao, Evanston, IL (US); Gonghu Li, New Haven, CT (US); Kimberly Gray, Evanston, IL (US); Richard M Lueptow, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 1586 days.

(21) Appl. No.: 12/152,481

(22) Filed: May 14, 2008

(65) Prior Publication Data

US 2009/0175757 A1    Jul. 9, 2009

Related U.S. Application Data

(60) Provisional application No. 60/930,082, filed on May 14, 2007.

(51) Int. Cl.
*A61L 9/20* (2006.01)
*B01D 67/00* (2006.01)
*B01D 65/08* (2006.01)
*B01D 69/14* (2006.01)
*B01D 71/02* (2006.01)
(Continued)

(52) U.S. Cl.
CPC ............... *A61L 9/205* (2013.01); *B01D 65/08* (2013.01); *B01D 67/0004* (2013.01); *B01D 67/0041* (2013.01); *B01D 67/0072* (2013.01); *B01D 69/141* (2013.01); *B01D 71/02* (2013.01); *B82Y 30/00* (2013.01); *C02F 1/32* (2013.01); *C02F 1/725* (2013.01); *C04B 35/46* (2013.01); *C04B 35/803* (2013.01); *C04B 41/009* (2013.01); *C04B 41/5041* (2013.01); *C04B 41/52* (2013.01); *C04B 41/87* (2013.01);

*C04B 41/89* (2013.01); *B01D 2321/168* (2013.01); *B01D 2325/12* (2013.01); *C02F 1/283* (2013.01); *C02F 1/444* (2013.01); *C02F 2305/10* (2013.01); *C04B 2111/00801* (2013.01); *C04B 2111/00827* (2013.01); *C04B 2235/526* (2013.01); *C04B 2235/5264* (2013.01); *C04B 2235/5288* (2013.01); *C04B 2235/5409* (2013.01); *C04B 2235/5445* (2013.01); *C04B 2235/5454* (2013.01)

(58) Field of Classification Search
None
See application file for complete search history.

(56) References Cited

U.S. PATENT DOCUMENTS 6,875,274 B2 *   4/2005   Wong et al. ................. 117/105
2006/0026996 A1 *  2/2006   Chen ........................ 65/374.13
(Continued)

OTHER PUBLICATIONS

Haremza et al, Attachment of single cdse nanosrystals to individual single walled carbon nanotubes, 2002, nano letters, vol. 2 No. 11, pp. 1253-1258.*

(Continued)

*Primary Examiner* — Melvin C Mayes
*Assistant Examiner* — Stefanie Cohen
(74) *Attorney, Agent, or Firm* — Casimir Jones S.C.

(57) ABSTRACT

The present invention provides titanium dioxide/single-walled carbon nanotube composites ($TiO_2$/SWCNTs), articles of manufacture, and methods of making and using such composites. In certain embodiments, the present invention provides membrane filters and ceramic articles that are coated with $TiO_2$/SWCNT composite material. In other embodiments, the present invention provides methods of using $TiO_2$/SWCNT composite material to purify a sample, such as a water or air sample.

19 Claims, 12 Drawing Sheets

(51) Int. Cl.
| | |
|---|---|
| B82Y 30/00 | (2011.01) |
| C02F 1/32 | (2006.01) |
| C02F 1/72 | (2006.01) |
| C04B 35/46 | (2006.01) |
| C04B 35/80 | (2006.01) |
| C04B 41/00 | (2006.01) |
| C04B 41/50 | (2006.01) |
| C04B 41/52 | (2006.01) |
| C04B 41/87 | (2006.01) |
| C04B 41/89 | (2006.01) |
| C02F 1/28 | (2006.01) |
| C02F 1/44 | (2006.01) |
| C04B 111/00 | (2006.01) |

(56) References Cited

U.S. PATENT DOCUMENTS

2006/0226763 A1\* 10/2006 Moon et al. .................. 313/495
2008/0242785 A1\* 10/2008 Ma et al. ....................... 524/413

OTHER PUBLICATIONS

Haberecht et al, Carbon nanostructures on high temperature ceramics—a novel composite material and its functionalization, 2005, catalysis today, vols. 102-103, pp. 40-44.\*
Sun et al, Attachment of inorganic nanoparticles onto carbon nanotubes, 2006, j electroceram, vol. 17, pp. 91-94.\*
Dechakiatkrai et al, Photocatalytic Oxidation of Methanol Using Titanium Dioxide/Single-Walled Carbon Nanotube Composite, Mar. 2007, Journal of the Electrochemical Society, 154 (5) A407-A411.\*
Agrios et al., "Photocatalytic transformation of 2,4,5-trichlorophenol on $TiO_2$ under sub-band-gap illumination" 2003 Langmuir 19, 1402-1409.
Anpo et al., "In situ photoluminescence of titania as a probe of photocatalytic reactions" 1989 Journal of Physical Chemistry B 93, 7300-2.
Arana et al., "$TiO_2$ activation by using activated carbon as a support. Part I. Surface characterization and decantability study" 2003 Applied Catalysis, B: Environmental 44, 161-172.
Arana et al., "$TiO_2$ activation by using activated carbon as a support. Part II. Photoreactivity and FTIR study" 2003 Applied Catalysis, B: Environmental 44, 153-160.
Bickley et al., "A Structural Investigation of Titanium-Dioxide Photocatalysts" 1991 Journal of Solid State Chemistry 92, 178-190.
Bideau et al., "On the "immobilization" of titanium dioxide in the photocatalytic oxidation of spent waters" 1995 Journal of Photochemistry and Photobiology A: Chemistry 91, 137-144.
Boyd et al., "Plasmon-Assisted Chemical Vapor Deposition" 2006 Nano Letters 6, 2592-2597.
Burnside et al., "Self-Organization of $TiO_2$ Nanoparticles in Thin Films" 1998 Chem. Mater. 10, 2419-2425.
Chen et al., "A comparative study on physicochemical properties and photocatalytic behavior of macroporous $TiO_2$-P25 composite films and macroporous $TiO_2$ films coated on stainless steel substrate" 2007 Applied Catalysis, A: General 317, 129-137.
Chen et al., "Fabricating Highly Active Mixed-Phase $TiO_2$ Photocatalysts by Reactive DC Magnetron Sputter Deposition" 2006 Thin Solid Film 515, 1176-1181.
Chen et al., "Preparation of a Novel $TiO_2$-Based p-n Junction Nanotube Photocatalyst" 2005 Environmental Science and Technology 39, 1201-1208.
Elser et al., "Particles Coming Together: Electron Centers in Adjoined $TiO_2$ Nanocrystals" 2006 Journal of Physical Chemistry B 110, 7605-7608.
Fan et al., "Anatase $TiO_2$-coated multi-wall carbon nanotubes with the vapor phase method" 2006 Journal of the American Ceramic Society 89, 731-733.
Feng et al., "Optical and electrical characterizations of nanocomposite film of titania adsorbed onto oxidized multiwalled carbon nanotubes" 2005 Journal of Physics: Condensed Matter 17, 4361-4368.
Fujihara et al., "Time-resolved photoluminescence of particulate $TiO_2$ photocatalysts suspended in aqueous solutions" 2000 Journal of Photochemistry and Photobiology, A: Chemistry 132, 99-104.
Fujishima et al., "Titanium dioxide photocatalysis: present situation and future approaches" 2006 Comptes Rendus: Chimie 9, 750-760.
Guo et al., "Sol gel derived photocatalytic porous $TiO_2$ thin films" 2005 Surface & Coatings Technology 198, 24-29.
Hurum et al. "Explaining the enhanced photocatalytic activity of Degussa P25 mixed-phase $TiO_2$ using EPR" 2003 Journal of Physical Chemistry B 107, 4545-4549.
Hurum et al., "Probing reaction mechanisms in mixed phase $TiO_2$ by EPR" 2006 Journal of Electron Spectroscopy and Related Phenomena 150, 155-163.
Jang et al., "Incorporation of Functionalized Single-Wall Carbon Nanotubes in Dye-Sensitized $TiO_2$ Solar Cells" 2004 Langmuir 20, 9807-9810.
Jitianu et al., "Synthesis and characterization of carbon nanotubes-$TiO_2$ nanocomposites" 2004 Carbon 42, 1147-1151.
Kamat "Photoinduced transformations in semiconductor-metal nanocomposite assemblies" 2002 Pure and Applied Chemistry 74, 1693-1706.
Kang et al., "Composite of carboxyl-modified multi-walled carbon nanotubes and $TiO_2$ nanoparticles: preparation and photocatalytic activity" 2007 Fullerenes, Nanotubes, and Carbon Nanostructures 15, 81-88.
Kim et al., "Rutile $TiO_2$-modified multi-wall carbon nanotubes in $TiO_2$ film electrodes for dye-sensitized solar cells" 2006 Journal of Applied Electrochemistry 36, 1433-1439.
Kis et al., "Reinforcement of single-walled carbon nanotube bundles by intertube bridging" 2004 Nature Materials 3, 153-157.
Klimova et al., "Characterization of $Al_2O_3$-$ZrO_2$ mixed oxide catalytic supports prepared by the sol-gel method" 1998 Microporous and Mesoporous Materials 20, 293-306.
Kongkanand et al., "Single Wall Carbon Nanotube Scaffolds for Photoelectrochemical Solar Cells. Capture and Transport of Photogenerated Electrons" 2007 Nano Letters 7, 676-680.
Lee et al., "Inactivation of bacterial endospores by photocatalytic nanocomposites" 2005 Colloids and Surfaces, B: Biointerfaces 40, 93-98.
Li et al., "Synthesizing mixed-phase $TiO_2$ nanocomposites using a hydrothermal method for photo-oxidation and photoreduction applications" 2008 Journal of Catalysis 253, 105-110.
Li et al., "The Solid-Solid Interface: Explaining the High and Unique Photocatalytic Reactivity of $TiO_2$-Based Nanocomposite Materials" 2007 Chemical Physics 339, 173-187.
Poyato et al., "Aqueous colloidal processing of single-wall carbon nanotubes and their composites with ceramics" 2006 Nanotechnology 17, 1770-1777.
Rajeshwar et al., "Semiconductor-based composite materials: Preparation, properties, and performance" 2001 Chemistry of Materials 13, 2765-2782.
Ridley et al., "Characterization and Surface-Reactivity of Nanocrystalline Anatase in Aqueous Solutions" 2006 Langmuir 22, 10972-10982.
Robel et al., "Single-walled carbon nanotube-CdS nanocomposites as light-harvesting assemblies: Photoinduced charge-transfer interactions" 2005 Advanced Materials (Weinheim, Germany) 17, 2458-2463.
Salvetat et al., "Elastic modulus of ordered and disordered multiwalled carbon nanotubes" 1999 Advanced Materials 11, 161-165.
Thostenson et al., "Advances in the science and technology of carbon nanotubes and their composites: a review" 2001 Composites Science and Technology 61, 1899-1912.
Wang et al. "Photocatalytic degradation of phenol on MWNT and titania composite catalysts prepared by a modified sol-gel method" 2005 Applied Catalysis, B: Environmental 56, 305-312.
Wang et al., "Photogeneration of Highly Amphiphilic $TiO_2$ Surfaces" 1998 Advanced Materials 10, 135-138.

(56) References Cited

OTHER PUBLICATIONS

Xu et al., "The absolute energy positions of conduction and valence bands of selected semiconducting minerals" 2000 American Mineralogist 85, 543-556.

Yao et al., Photoreactive TiO2/Carbon Nanotube Composites: Synthesis and Reactivity. Environmental Science & Technology, 2008, 42, 4952-4957.

Yoo et al., "Synthesis of anatase nanostructured TiO2 particles at low temperature using ionic liquid for photocatalysis" 2006 Catalysis Communications 6, 259-262.

Yu et al., "Enhancement of adsorption and photocatalytic activity of TiO2 by using carbon nanotubes for the treatment of azo dye" 2005 Applied Catalysis, B: Environmental 61, 1-11.

Yu et al., "Preparation and characterization of aligned carbon nanotubes coated with titania nanoparticles" 2006 Chinese Science Bulletin 51, 2294-2296.

Zhang et al., "Fixed-bed photocatalysts for solar decontamination of water" 1994 Environmental Science and Technology 28, 435-42.

Zhang et al., "Role of Particle Size in Nanocrystalline TiO2-Based Photocatalysts" 1998 Journal of Physical Chemistry B 102, 10871-10878.

Zhang et al., "Room-Temperature Preparation of Nanocrystalline TiO2 Films and the Influence of Surface Properties on Dye-Sensitized Solar Energy Conversion" 2006 J. Phys. Chem. B 110, 21890-21898.

* cited by examiner (a)

(b)

(c)

TITANIUM DIOXIDE, SINGLE-WALLED CARBON NANOTUBE COMPOSITES

The present application claims priority to U.S. provisional application 60/930,082, filed May 14, 2007, which is herein incorporated by reference in its entirety.

This invention was made with government support under Grant No. BES-0403581 awarded by the National Science Foundation and Grant Nos. DE-FG02-03ER15457/A003 and DE-AC02-06CH11357 awarded by the U.S. Department of Energy. The government has certain rights in the invention.

FIELD OF THE INVENTION

The present invention relates to titanium dioxide/single-walled carbon nanotube composites ($TiO_2$/SWCNTs), articles of manufacture, and methods of making and using such composites. In certain embodiments, the present invention provides membrane filters and ceramic articles that are coated with $TiO_2$/SWCNT composite material. In other embodiments, the present invention provides methods of using $TiO_2$/SWCNT composite material to purify a sample, such as a water or air sample.

BACKGROUND $TiO_2$ photocatalysis has been extensively studied for the removal of organic contaminants in water or air (1-11). Mixed-phase $TiO_2$-based composites tend to show higher photoreactivity in comparison to pure-phase materials, as exhibited by commercial Degussa P25, due to the formation of solid-solid interfaces that facilitate charge transfer and spatial separation, reduced electron-hole recombination, and interfacial defect sites that act as catalytic "hot spots" (2-7).

Recently, efforts to combine $TiO_2$ with activated carbon (12, 13) or carbon nanotubes (CNTs) in simple mixtures or as nanocomposite materials sought to create more highly reactive photocatalysts (14-18). The synthesis of $TiO_2$/CNT nanocomposites using sol-gel, chemical vapor deposition (CVD), and physical vapor deposition (PVD) methods has been reported (17, 19-21). The addition of multi-walled CNTs (MWCNTs), prepared by a catalytic deposition method, to a slurry of Degussa P25 improved color removal in an aqueous solution of azo-dyes under ultraviolet light (16). The researchers, however, did not fully explain how a simple mixture of $TiO_2$ and MWCNTs would interact to accelerate the decay of the dye. MWCNTs coated with a uniform layer of anatase $TiO_2$ using a modified sol-gel process displayed a higher rate of phenol degradation in water than either of the components alone or in simple mixtures (14). The authors proposed that the MWCNTs served as a catalyst support increasing the reactive surface area of the $TiO_2$ in suspension and suggested that intimate interphase contact between the $TiO_2$ and MWCNTs has other synergistic photochemical effects. MWCNTs coated with anatase using a sol-gel method showed high photocatalytic inactivation of bacterial endospores dispersed in water (15). The authors indicated that the MWCNTs not only provided a large surface area support for the titania catalyst, but also stabilized the charge separation by trapping the electrons transferred from $TiO_2$, thereby hindering charge recombination.

Previous work, then, illustrates that there are a variety of ways to combine $TiO_2$ and CNTs to create a photocatalyst. The structure of the CNTs in combination with $TiO_2$, however, is not clear. For example, $TiO_2$ nanoparticles and CNTs may be combined in a random composite, as shown in FIG. 1(a), or CNTs may be coated with $TiO_2$ nanoparticles, as shown in FIG. 1(b). In both cases, CNTs disperse the $TiO_2$, increasing the reactive surface area. Furthermore, given the conducting and semiconducting properties of CNTs, it is also possible that photoexcited electrons from $TiO_2$ may be transferred to the CNTs to hinder recombination and enhance oxidative reactivity.

SUMMARY OF THE INVENTION

The present invention provides titanium dioxide/single-walled carbon nanotube composites ($TiO_2$/SWCNTs), articles of manufacture, and methods of making and using such composites. In certain embodiments, the present invention provides membrane filters and ceramic articles that are coated with $TiO_2$/SWCNT composite material. In other embodiments, the present invention provides methods of using $TiO_2$/SWCNT composite material to purify a sample, such as a water or air sample.

In some embodiments, the present invention provides compositions comprising: $TiO_2$ particles and single-walled carbon nanotubes (SWCNTs). In certain embodiments, the $TiO_2$ particles are anatase nanoparticles. In further embodiments, the average diameter of the $TiO_2$ particles is between about 75 and 175 nm (e.g., between 90-150 nm, or between 100-145, or between 120-140). In particular embodiments, the ratio of the $TiO_2$ particles to the SWCNTs is between 8:1 to 125:1 (e.g., 10:1, 15:1; 20:1, 35:1, 50:1, 65:1, 75:1, 100:1, 110:1, or 120:1). In certain embodiments, the $TiO_2$ particles and single-walled carbon nanotubes (SWCNTs) are in a composite that is chemically reactive (e.g. photoreactive when exposed to ultraviolet light, or reactive to the application of certain molecules).

In further embodiments, the average diameter of the SWCNTs is about 0.5-3.0 nm (e.g., 1.0-2.5, 1.3-1.5, or about 1.4). In some embodiments, the SWCNTs are about 0.3 to about 4.0 µm in length (e.g., 0.5-3.0, 1.0-2.5, or 1.5-2.0). In certain embodiments, the compositions of the present invention further comprise ceramic material (e.g., ceramic disks, solar cell components, bio-medical components, etc.). In other embodiments, the ceramic material comprises alumina or $ZrO_2$.

In particular embodiments, the present invention provides articles of manufacture comprising: a membrane filter, wherein the membrane filter comprises a composite material, wherein the composite material comprises $TiO_2$ particles and single-walled carbon nanotubes (SWCNTs). In some embodiments, the membrane filter is composed of ceramic material. In further embodiments, the ceramic comprises alumina or $ZrO_2$.

In additional embodiments, the present invention provides methods of making a chemically reactive (e.g., photoreactive) $TiO_2$/SWCNT composite comprising: a) dispersing single-walled carbon nanotubes (SWCNTs) in water to generate a suspension; b) mixing $TiO_2$ particles into the suspension; c) treating the suspension under conditions such that a dehydrated suspension is generated; and d) drying the dehydrated suspension under conditions such that a chemically reactive (e.g., photoreactive) $TiO_2$/SWCNT composite is generated.

In certain embodiments, the ratio of the $TiO_2$ particles to the SWCNTs in the $TiO_2$/SWCNT composite is from 8:1 to 125:1. In some embodiments, the treating step comprises heating the suspension. In further embodiments, the drying step comprises maintaining the dehydrated suspension at an elevated temperature for at least 5 hours (e.g., in an oven or similar device). In further embodiments, the method further comprises a step before step b) of sonicating the suspension.

In some embodiments, the present invention provides methods of treating a substrate (e.g., fluid) comprising; a) providing a composite material comprising $TiO_2$ particles and single-walled carbon nanotubes (SWCNTs); b) contacting the composite material with a substrate (e.g., fluid) comprising organic contaminants; and c) activating (e.g., photoactivating or chemically activating) the composite material under conditions such that at least a portion of the organic contaminants in the substrate are altered. In certain embodiments, the organic contaminant are altered by being inactivated, destroyed, or converted into a non-contaminant. In further embodiments, the substrate comprises water (e.g., waste water, water to be treated for public consumption, or industrial discharge water). In particular embodiments, the substrate comprises air (e.g., air passing through a room air filtration system, air used in an industrial process, etc.). In other embodiments, the methods further comprise providing a membrane filter, wherein the composite material is located on and/or within the membrane filter. In further embodiments, the photoactivating comprises exposing the composite material to ultraviolet illumination or other type of light.

In certain embodiments, the present invention provides methods of making a chemically reactive (e.g., photoreactive) article (e.g., ceramic article or other base article) comprising: a) mixing a composite material in water to generate a suspension, wherein the composite material comprises $TiO_2$ particles and single-walled carbon nanotubes (SWCNTs); b) applying at least a portion of the suspension to an article; and c) heating the ceramic article under conditions such that a chemically reactive (e.g., photoreactive) article is generated which comprises a layer of $TiO_2$/SWCNT composite.

In some embodiments, the suspension has a pH between 3.0 and 7.0 (e.g., 3.0, 4.0, 5.0, 6.0, and 7.0). In further embodiments, the ceramic article comprises a ceramic disc (e.g., a porous ceramic disc for filtering material). In certain embodiments, the ceramic article comprises a plurality of ceramic particles (e.g., micro or nano particles). In other embodiments, the ceramic article is dipped into the suspension. In particular embodiments, the ceramic article comprises $ZrO_2$.

In particular embodiments, the composite of the present invention are employed in dye-sensitized solar cells to enhance the electron transfer in the $TiO_2$ electrodes. As such, in some embodiments, the present invention provides solar cells comprising the composites of the present invention.

In other embodiments, the composites of the present invention are used to retard biological and/or chemical fouling of materials susceptible to such fouling, such as membranes, containers, or other surfaces. In still other embodiments, the present invention provides a TiO2/SWCNT composite coating that is applied to a surface to reduce or prevent the build-up or fouling with chemical or biological materials on the surface. As such, in certain embodiments, the present invention provides materials (e.g., membranes) that comprise the composites of the present invention (e.g., for use in biological and/or chemical processes). In some embodiments, the composites of the present invention coat a surface of such material, and in other embodiments, the composites of the present invention are within the surfaces (e.g., form part of the material). In certain embodiments, such materials are used with equipment, such as dialysis equipment and related filtering systems.

In some embodiments, the present invention provides methods of reducing fouling of an article comprising; a) providing an article subject to biological or chemical fouling, wherein the article comprises a composite material comprising $TiO_2$ particles and single-walled carbon nanotubes (SWCNTs); b) contacting the article with a substrate comprising organic contaminants; and c) activating (e.g., chemically or photo activating) the composite material under conditions such that at least a portion of the organic contaminants in said substrate are altered, thereby reducing or preventing fouling of the article. In particular embodiments, the article comprises a membrane. In further embodiments, the organic contaminant are altered by being inactivated, destroyed, or converted into a non-contaminant.

In some embodiments, the present invention provides methods of depositing a well-dispersed coating of small particles on a surface article comprising; a) mixing a composite material in water to generate a suspension, wherein said composite material comprises $TiO_2$ particles and single-walled carbon nanotubes (SWCNTs); b) applying at least a portion of said suspension to an article; and c) heating said article under conditions such that a chemically reactive article is generated which comprises a layer of TiO2/SWCNT composite. In particular embodiments, the article is a ceramic article.

In further embodiments, the present invention provides a chemically reactive apparatus that can come into contact with a fluid comprising; a) a base or substrate material; and b) a layer of TiO2/SWCNT composite. In particular embodiments, the base or substrate material is ceramic. In further embodiments, the fluid contains biological or chemical contaminants (e.g., bacteria). In some embodiments, the biological or chemical contaminants in said fluid are altered. In certain embodiments, the biological or chemical contaminants are altered by being inactivated, destroyed, or converted into a non-contaminant. In further embodiments, the exposing the composite material to ultraviolet illumination results in photoactivation. In particular embodiments, the attachment of biological or chemical contaminants in the fluid to the composite layer is reduced or eliminated.

DESCRIPTION OF THE DRAWINGS

FIG. 7A shows the water purification set up from Example 2 employing the TiO2/SWCNT composites layered on a ceramic filter, while FIG. 7B shows the results from Example 2 where the filter (as well as those coated with only $TiO_2$ or only P25) was employed with ultraviolet activation to remove phenol from water.

DETAILED DESCRIPTION

The present invention provides titanium dioxide/single-walled carbon nanotube composites ($TiO_2$/SWCNTs), articles of manufacture, and methods of making and using such composites. In certain embodiments, the present invention provides membrane filters and ceramic articles that are coated with $TiO_2$/SWCNT composite material. In other embodiments, the present invention provides methods of using $TiO_2$/SWCNT composite material to purify a sample, such as a water or air sample.

Figure 1:
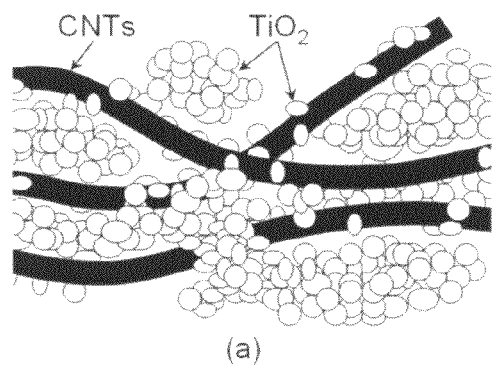
FIG. 1 shows schematics of $TiO_2$/CNT composite structures: a) a composite made up of a random mixture of nanoparticulate $TiO_2$ and CNTs, b) CNTs coated with small $TiO_2$ nanoparticles, and c) CNTs wrapped around large $TiO_2$ nanoparticles.
Figure 1:
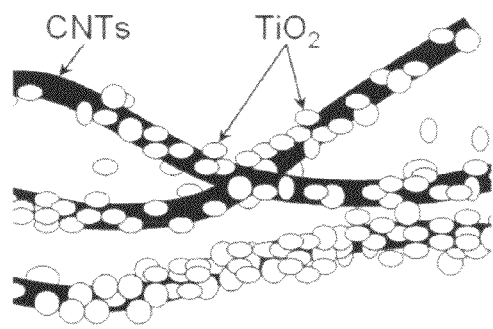
Figure 1:
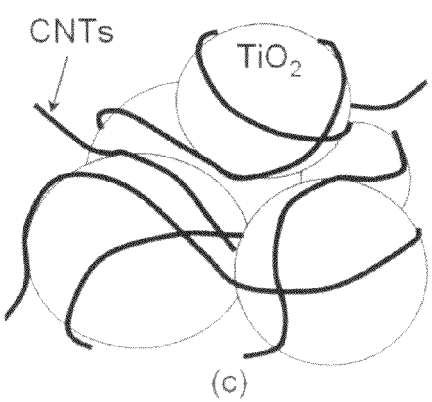

In developing embodiments of the present invention, a composite structure has been developed in which SWCNTs (single-walled carbon nanotubes) (or bundles) decorate and bridge between the surfaces of relatively large $TiO_2$ particles (e.g., 100-150 nm or so in diameter, as shown in FIG. 1C). The present invention is not limited to a particular mechanism. Indeed, an understanding of the mechanism is not necessary to practice the present invention. Nonetheless, it is contemplated that the SWCNTs used in these composites create interphase connections allowing electron transfer from the $TiO_2$ to the SWCNT leading to enhanced photo-reactivity. Certain illustrative embodiments of the invention are described below. The present invention is not limited to these embodiments.

In developing embodiments of the present invention, four types of composites of $TiO_2$ (anatase phase) and carbon nanotubes (CNTs) were prepared using an evaporation and drying process. Two sizes of anatase $TiO_2$ were used: 5 nm nanoparticles (denoted S-anatase) and 130 nm microparticles (denoted L-anatase). Both single-wall carbon nanotubes (SWCNTs) and multi-walled carbon nanotubes (MWCNTs) were compared for their effectiveness (note that previous researchers only considered MWCNTs). To prepare a composite photocatalyst, CNTs and anatase $TiO_2$ powder were added to a beaker of water while stirring. After evaporating the water, the remaining powder was dried. The SEM image (FIG. 2) shows the L-anatase/SWCNT composite. The long strands of SWCNT bundles are dispersed and interwoven among the L-anatase particles.

Figure 3:
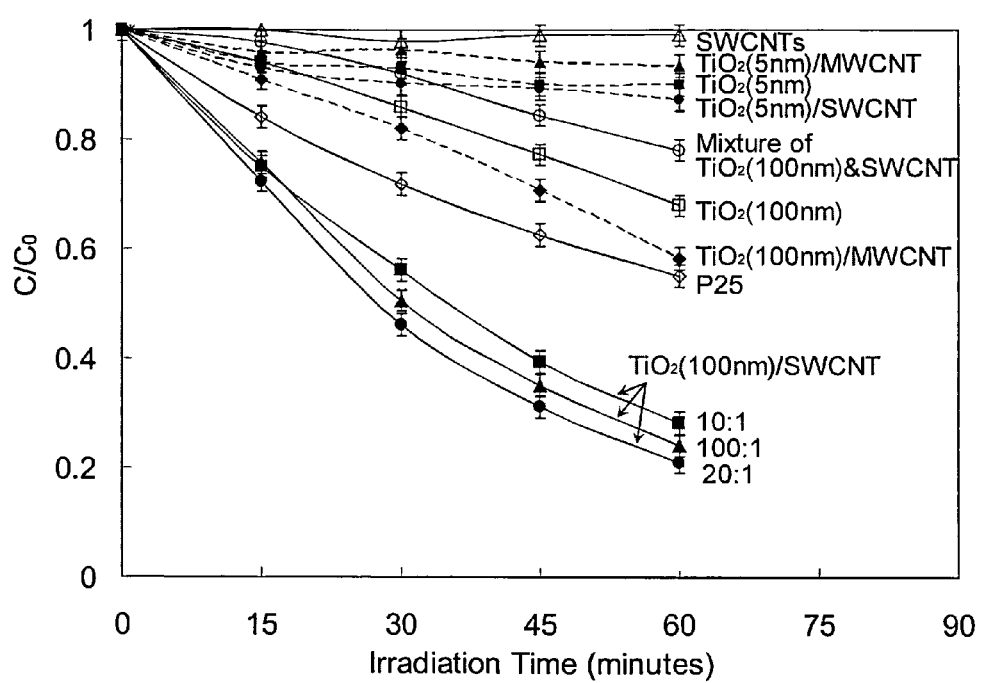
FIG. 3 shows a comparison of the photocatalytic decay of phenol for various anatase/CNT composites and controls. The $TiO_2$/CNT mass ratio was 20:1 unless otherwise indicated. Each data point represents the average of 2-4 replicate concentration measurements C, where Co is the initial concentration. Error bars represent one standard deviation.

The reactivity of the photocatalysts, for example, was compared using phenol degradation tests. In each test, 10 mg of photocatalyst composite was dispersed as a suspension in 100 ml phenol solution with an initial concentration of 400 μM. The suspension was illuminated with a mercury UV lamp and samples were taken every 15 minutes for 60 minutes. The phenol concentrations of the samples were measured with a High Performance Liquid Chromatography. FIG. 3 shows the phenol degradation kinetics for the photocatalysts and controls in terms of the percentage of the initial phenol concentration remaining (C/CO) as a function of time. Pure SWCNTs, pure S-anatase, and S-anatase/MWCNT composites show poor degradation (the value for C/CO remains high as time goes on). Pure L-anatase, L-anatase/MWCNT composites, and a simple mixture (as opposed to composite) of L-anatase and MWCNTs show some degradation of the phenol, comparable to P25 $TiO_2$, a recognized standard photocatalyst, consistent with previous results indicating that P25 is more reactive than pure phase $TiO_2$.

L-anatase/SWCNT composites show much faster degradation than any other catalyst. This is evident in the low concentrations (low values of C/CO) after irradiation for 60 minutes.

Work conducted during the development of embodiments of the present invention also showed that SWCNTs can substantially improve the uniformity and coverage of $TiO_2$ coatings on porous $ZrO_2$ membranes. The $ZrO_2$ membranes were dip-coated with anatase $TiO_2$, $TiO_2$/SWCNT composite, $TiO_2$+SWCNT mixture, and $TiO_2$/MWCNT composite, at pH 3, 5 and 8. The $TiO_2$/SWCNT composite forms a complete and uniform coating at pH 5 (~100% coverage). The $TiO_2$+SWCNT mixture and $TiO_2$/MWCNT composite also promote better coverage than $TiO_2$ alone. No improvement was observed for a $TiO_2$/surfactant (Triton X-100) coating.

EXAMPLES

The following Examples are presented in order to provide certain exemplary embodiments of the present invention and are not intended to limit the scope thereof.

Example 1

Photoreactive Composites Composed of Single-Walled Carbon Nanotubes and $TiO_2$

Electron-hole recombination limits the efficiency of $TiO_2$ photocatalysis. This Example investigates the efficacy with which anatase/carbon nanotube (CNT) composite materials reduce charge recombination and enhance reactivity. Nanostructured assemblies were synthesized which were composed of different proportions of anatase (5 or 100 nm) and either single- or multi-walled CNTs. The composites were prepared using a simple low temperature process in which CNTs and anatase nanoparticles were dispersed in water, dehydrated at 80° C., and dried at 104° C. The structures of the various $TiO_2$/CNT composites were characterized by scanning electron microscopy (SEM) and their function was tested by phenol oxidation. Charge recombination was compared by measuring the photoluminescence spectra of select composites. It was found that a nanostructured composite assembled from the 100 nm anatase and single-walled CNTs (SWCNTs) exhibited enhanced and selective photocatalytic oxidation of phenol in comparison to both pure anatase and Degussa P25. While the present invention is not limited to any particular mechanism, and an understanding of the mechanism is not necessary to practice the present invention, it is believed that electrons are shuttled from $TiO_2$ particles to the SWCNTs as a result of an optimal $TiO_2$/CNT arrangement that stabilizes charge separation and reduces charge recombination. In addition, it is believed that the SWCNT assembly provides better catalyst support (dispersal and connection) than multi-walled CNTs.

Materials and Methods

Three types of $TiO_2$ were employed: large anatase nanoparticles (nominally 100 nm, but actually 130 nm), small anatase nanoparticles (5 nm), and mixed-phase Degussa P25 (50 nm). Commercially prepared SWCNTs (1.4 nm diameter and 0.5-3.0 μm long) and MWCNTs (20-30 nm diameter and ~30 μm length) were treated in a reflux system with nitric acid to functionalize the nanotubes (14, 15, 22). More specific details on the materials are described below.

Anatase powders (Analytical Grade) were purchased from Sigma-Aldrich (products #637254 and #232033). According to the manufacturer, the average larger particle size is 100 nm. Based on SEM images that were generated, however, the particle diameters range from 40 nm to 300 nm, with an average diameter of 130 nm and standard deviation of ~70 nm. The BET surface area was measured to be 8.6 m2/g. It is difficult to measure the size of the smaller anatase powders, but according to the manufacturer they have an average particle size of 5 nm and a reported average BET surface area of approximately 240 m2/g. SEM results showed that the particles tend to form large aggregates with sizes ranging from several hundred nanometers to about two microns. X-ray diffraction confirms that both of the $TiO_2$ powders are pure phase anatase. The performance of the $TiO_2$/CNT composites was compared to that of Degussa P25 powders (Evonik Degussa), which have a nominal particle size of about 50 nm, but also tend to form large aggregates ranging from hundreds of nanometers to several microns. MWCNTs (NanoTech Labs Inc.) were commercially prepared using chemical vapor deposition and prior to use were treated in a reflux system with concentrated nitric acid (70%) at ~150° C. for 1 hour, filtered on a glass fiber membrane (0.45 μm pore size), and dried at 60° C. Acid treatment of CNTs tends to functionalize the nanotube walls, which may enhance the adsorption of $TiO_2$ or organic compounds on the CNTs (14,15,22). According to the manufacturer, the MWCNTs have a purity greater than 90%, a diameter of 20-30 nm, and a length of ~30 μm. SWCNTs (Carbon Solutions, Inc.) were commercially synthesized by electric arc discharge using a Ni/Y catalyst and then were treated in a concentrated nitric acid reflux system to remove the Ni/Y catalyst and amorphous carbon impurities. According to the manufacturer, the individual tubes are 0.5-3.0 μm long and have an average diameter of 1.4 nm. They tend to occur as bundles with bundle lengths of 1-5 μm and average bundle diameters of 2-10 nm.

Anatase/CNT composite structures were prepared by a simple evaporation and drying process. First, approximately 10 mg CNTs were dispersed in water in a 150 ml beaker and sonicated for 10 minutes. $TiO_2$ powder was added to the suspension while stirring. After additional sonication for 10 minutes, the suspension containing CNTs and $TiO_2$ particles was heated to 80° C. on a stir plate with air flowing across the suspension's surface to accelerate the evaporation of water. After the water evaporated, the composite was dried overnight in an oven at 104° C. to avoid oxidation of the SWCNTs that occurs at higher temperatures in the presence of oxygen. Composites were made at $TiO_2$ to CNTs mass ratios of 10:1, 20:1, and 100:1 in batches of approximately 200 mg of nanocomposite. Four types of composites were prepared: $TiO_2$ (100 nm)/SWCNT (10:1, 20:1, and 100:1 mass ratios); $TiO_2$ (100 nm)/MWCNT (20:1, and 100:1 mass ratios); $TiO_2$ (5 nm)/SWCNT (20:1 mass ratios); and $TiO_2$ (5 nm)/MWCNT (20:1 mass ratios).

The reactivity of the photocatalysts was measured by phenol degradation. In each test, 10 mg of photocatalyst composite was dispersed in 100 ml 400 μM phenol solution. To allow the adsorption of phenol on the catalyst the suspension was stirred for 20 minutes under dark conditions. Then the suspension was illuminated with a mercury UV lamp. Samples were taken every 15 minutes and the phenol concentration was measured by High Performance Liquid Chromatography (HPLC). For all the photocatalysts tested, the initial change in concentration during this 20-minute equilibration time was less than 3%. The solution was illuminated with a mercury UV lamp (100 W, B-100 AP from UVP, Inc.), which has strong emission lines at 366, 436, and 549 nm. The distance between the lamp and the phenol solution was ~10 cm and the light intensity at the surface of the solution was 170 μM·m-2·s−1 (photon flux). The tests were conducted inside a large, enclosed box at 24° C. The lamp heated the phenol solution to about 32° C. during the test. A sample taken immediately after turning on the UV light served as the initial concentration (CO). Thereafter, samples were taken every 15 minutes for 60 minutes. A sample volume of 1.5 ml was filtered through a glass fiber filter (0.2 μm pore size) to remove the catalyst prior to analysis. The phenol concentrations of the samples were measured by High Performance Liquid Chromatography (HITACHI HPLC, with L-4500 Diode Array Detector, D-6000 Interface and L-6200A Intelligent Pump) using a SUPELCO-SIL LC-18 HPLC column with 0.5 ml/min flow rate and a mixture of methanol and water with 1 wt % acetic acid (7:3 in volume) as the mobile phase (23). Typical aromatic by-products of phenol degradation were measured through the same column with 1 ml/min flow rate and a mobile phase of potassium monohydrogen phosphate solution, methanol, and THF (tetrahydrofuran) mixture as reported elsewhere (24). For the measurement of nonaromatic organic acids, an Aminex HPX-87H Ion Exchange Column was used with 0.6 ml/min flow rate and 0.005 M sulfuric acid as the mobile phase (25). Tests were conducted 2-4 times, and the results were repeatable to within less than 0.04 in terms of the normalized concentrations. The total organic carbon levels were measured using a TOC analyzer (Tekmar-DOHRMANN, APHA 5310B) (26).

Results and Discussion

1. Anatase/CNT Composites

Figure 2:
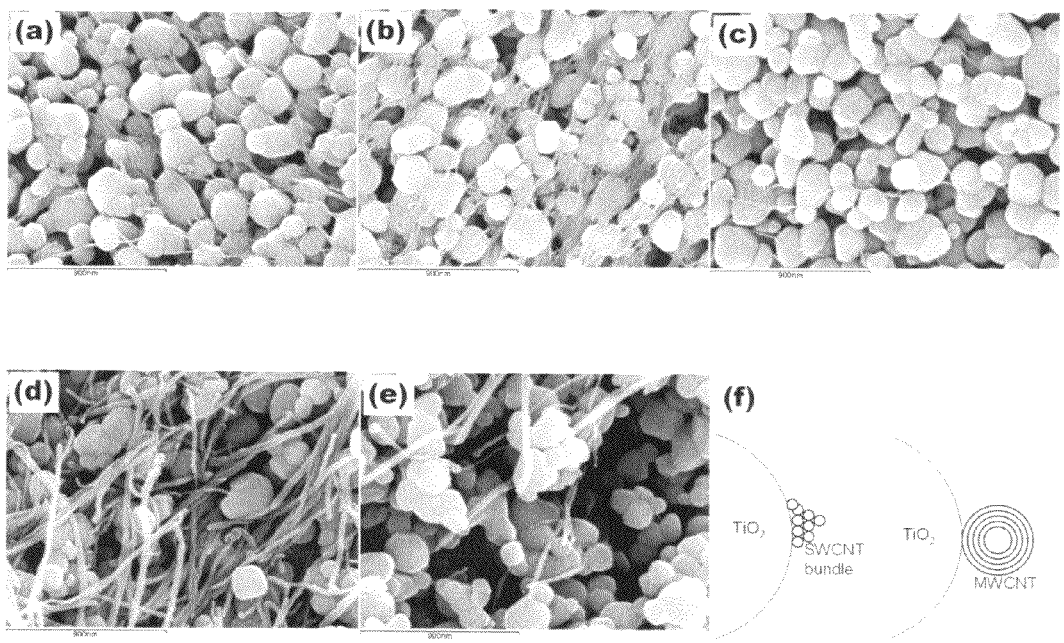
FIG. 2 shows SEM images of $TiO_2$ (100 nm)/SWCNT composites at mass ratios of 20:1 (a), 10:1 (b), 100:1 (c); $TiO_2$ (100 nm)/MWCNT composites at mass ratio of 20:1 (d) and 100:1 (e); and a schematic of a SWCNT bundle and a MWCNT in contact with a $TiO_2$ particle (not to scale) (f).

FIG. 2 shows the SEM images of the $TiO_2$ (100 nm)/CNT composites at the mass ratios considered. At the 20:1 mass ratio, the SWCNT bundles are well dispersed and inter-woven among the $TiO_2$ particles (FIG. 2(a)). The SWCNT bundles, which appear to be ~10 nm in diameter, wrap around the relatively larger anatase particles conforming to the schematic in FIG. 1(c), resulting in substantial contact with the particle surface. In FIG. 2(b) at a 10:1 mass ratio, more SWCNT bundles are in contact with one another, draping over and nearly covering some of the $TiO_2$ particles. At 100:1 (FIG. 2(c)), few SWCNT bundles are evident, but those that are visible are attached to and inter-woven among the $TiO_2$ particles. For comparison, in FIG. 2(d) the 20:1 $TiO_2$ (100 nm)/MWCNT composite is shown. The number concentration of MWCNTs in FIG. 2(d) appears greater than the SWCNT number concentration in FIG. 2(a) because of the lower mass density of the MWCNTs compared to SWCNTs. Also, the MWCNTs have a larger diameter (20-30 nm) than the SWCNT bundles. FIG. 2(e) provides an image of the 100:1 mass ratio for the MWCNT composite and illustrates a greater degree of anatase aggregation and less direct contact between the MWCNTs and the anatase particles. At the mass ratios tested and using the hydration/dehydration preparation technique, this example was unable to create composite structures for $TiO_2$ (5 nm)/SWCNT and $TiO_2$ (5 nm)/MWCNT by coating the nanotubes with the titania according to the conceptual picture shown in FIG. 1(b). Instead, the 5 nm anatase particles tend to form large aggregates around which the CNTs loosely loop.

From FIG. 2(a-e) it is evident that SWCNT bundles more easily bend and wrap around $TiO_2$ particles than MWCNTs. While the present invention is not limited to any mechanism, it is believed that this is because of the weak van der Waals interaction between the SWCNTs in a bundle. Since the SWCNTs can easily slide past each other, a low bending modulus (27) results compared to MWCNTs (28). In addition, as illustrated conceptually in FIG. 2(f), more contact points may be created between a bundle of SWCNTs and the $TiO_2$ surface than between a single MWCNT and $TiO_2$ particle.

Clearly, the $TiO_2$ (100 nm)/SWCNT composites shown in FIGS. 2(a-c) conform to the conceptual model shown in FIG. 1(c) and display a higher degree of individual contact and bridging than for $TiO_2$ (100 nm)/MWCNT composites or $TiO_2$ (5 nm)/CNT composites. These findings are consistent with a recent report that hydration and dehydration processing produces substantial contact among $TiO_2$ nanocrystals (29). Thus, the $TiO_2$ (100 nm)/SWCNT composite exhibits maximum interphase contact, suggesting higher chemical reactivity.

2. Phenol Oxidation

The anatase/CNT composite structures were tested to determine photocatalytic oxidation ability by comparing the decay of phenol among various anatase/CNT composites and corresponding controls, as shown in FIG. 3. Over the course of a 60-minute reaction time, no phenol loss was observed in the presence of either SWCNTs or MWCNTs alone at a loading of 10 mg/L. Thus, phenol adsorption to the CNT surface and volatile losses were negligible under these reaction conditions. Phenol decay in the 100 nm anatase slurry was about 30%, corresponding to a pseudo first order rate constant of 0.006 $min^{-1}$. The "P25" curve shows a better degradation rate with a rate constant (0.010 $min^{-1}$) that is roughly double that of the 100 nm anatase. While the conventional notion is that mixed-phase P25 is more reactive than pure $TiO_2$ phases, some of the enhanced activity may be associated with particle size differences, 130 nm (nominally 100 nm with a range of 40~300 nm) for anatase compared to 50 nm with a similar wide range of sizes due to heterogeneity and aggregation for P25 (30). While both $TiO_2$ powders show a wide and overlapping range of particle sizes, P25 displays a greater tendency to aggregate than the 100 nm anatase powders. Thus the effective surface areas of the two $TiO_2$ powders are probably similar, though difficult to accurately measure.

The "$TiO_2$ (100 nm)/SWCNT" decay curves show faster degradation (k=0.026 Min-1) than occurs with either $TiO_2$ (100 nm) or P25, indicating that the photocatalytic reactivity of the anatase powders is enhanced by their interaction with SWCNTs in the arrangement shown in FIGS. 1(c) and 2(a-c). Although the phenol degradation was quite good regardless of the ratio of anatase to SWCNTs, a ratio of 20:1 was optimal having a degradation rate approximately 2.5 times higher than P25 and more than 4 times higher than the anatase powder alone. Adding more SWCNTs (by changing the ratio from 20:1 to 10:1) did not increase the degradation rate, probably because a higher concentration of SWCNT bundles reduces the light intensity on the $TiO_2$ surfaces. The dried $TiO_2$ (100 nm)/SWCNT composites were observed under SEM after the phenol degradation tests and found to be visually identical to the images taken before the tests, suggesting no degradation of the composite structure.

In a previous report on anatase-MWCNT nanocomposites prepared using a sol-gel method (14), phenol degradation tests were conducted with a slightly higher initial concentration (~500 μM) and 10 times higher catalyst loading (1 g/L). About 50% phenol was remaining after 2 hours and 20% was remaining after 3 hours. In comparison, the $TiO_2$ (100 nm)/SWCNT composites of this Example showed much better photocatalytic activity (~20% remaining after 1 hour) at an order of magnitude lower catalyst loading.

Several control tests put these results in perspective. The curve marked "Mixture of $TiO_2$ (100 nm) & SWCNT" tested the performance of a simple mixture of SWCNT powder (1 mg) and 100 nm anatase powder (10 mg) dispersed in phenol solution directly without the hydration/dehydration processing to create a composite. The mixture had substantially lower reactivity than $TiO_2$ (100 nm)/SWCNT composites, clearly showing that when the nanotubes are simply dispersed in the suspension without close, interphase contact, phenol decay is not enhanced. In fact, the mixture showed a diminished reactivity relative to pure 100 nm $TiO_2$, likely because the suspended nanotubes partially block the UV light, slowing photodegradation. Thus, the hydration/dehydration process is an important step in the preparation of the closely coupled composites that display enhanced reactivity. It is important to note that the pure anatase powder processed through a similar hydration/dehydration cycle exhibits the same performance as the untreated anatase powder, indicating that the impact of the synthesis process is to create a nanocomposite, not to alter the inherent properties of the anatase powders.

The $TiO_2$ (100 nm)/MWCNT composite prepared by the same hydration/dehydration method showed a slightly better degradation rate than the pure anatase powders, consistent with previous reports about the synergistic effect between $TiO_2$ and MWCNTs (14-16). However, this improvement is small in comparison to that produced by the $TiO_2$ (100 nm)/SWCNT composites and is likely due to the structural differences between the SWCNTs and MWCNTs (FIG. 2). Finally, due to the high degree of particle aggregation and poor individual contact between the anatase particles and CNTs, the 5 nm anatase and its composites showed limited reaction with phenol (less than 10% decay in 1 hour).

3. Degradation By-Products

Figure 4:
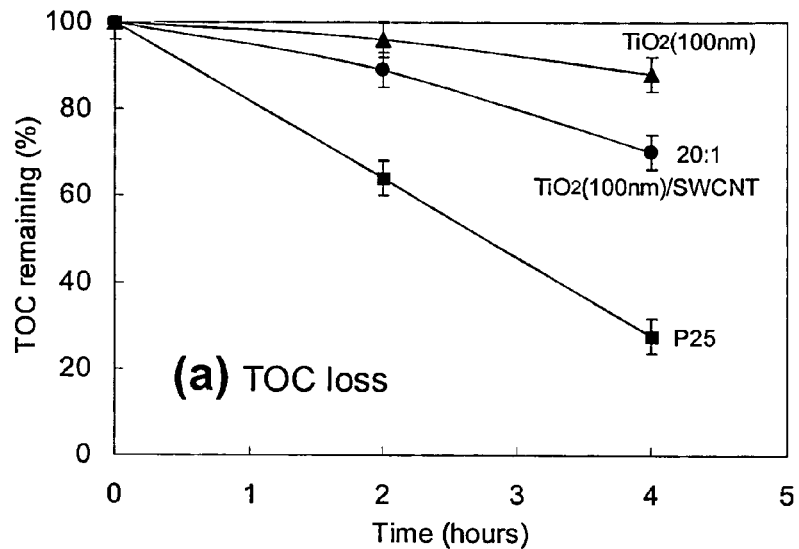
FIG. 4 shows a comparison of total organic carbon (TOC) loss (a) and oxalic acid decay (b) for pure-phase anatase (100 nm), the $TiO_2$ (100 nm)/SWCNT composite, and P25. The error bar represents one standard deviation based on 6 replicates.
Figure 4:
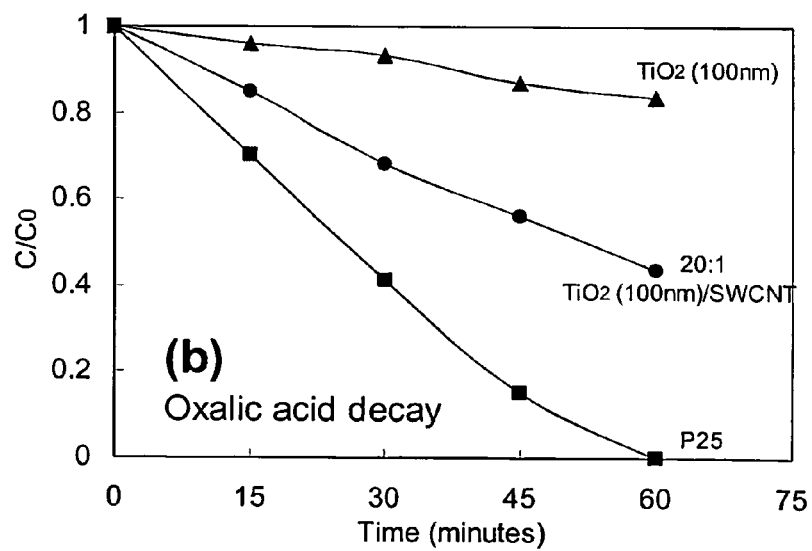

In order to compare the efficacy of the $TiO_2$ (100 nm)/SWCNT composite to mineralize phenol, specific aromatic and aliphatic oxidation products of phenol analyzed over longer reaction times and were the loss in total organic carbon concentration was monitored. As shown in FIG. 4(a), limited TOC loss (<10%) was produced photocatalytically by pure anatase over 4 hours of reaction. The incorporation of the anatase particles into a SWCNT composite improved phenol mineralization (30%), but the overall total organic carbon loss was far less than that produced by P25 (75%). Although the finding that P25 is a general and robust catalyst for organic mineralization is expected (1, 6), it was surprising that the anatase materials showed such limited mineralization. This is explained by their inability to oxidize phenol degradation by-products. In FIG. 4(b) shows photocatalytic decay of oxalic acid (2-butenecioic acid), one of the ring cleavage products in the oxidation of phenol (24). Pure anatase has low reactivity with this compound, whereas P25 produces complete degradation. The anatase/SWCNT composite displays better reactivity than pure anatase but only about half that of P25.

The major stable intermediates of phenol oxidation include hydroquinone, catechol, benzoquinone, maleic acid, oxalic acid, and formic acid (24). The proportions of phenol, hydroquinone, catechol, maleic acid, oxalic acid, and mineralized carbon after 2 and 4 hours of UV illumination were measured. At both sampling times, these by-product concentrations account for 55% to 60% of the total carbon mass in the system, and it is believed that the balance is comprised of various aliphatic ring-cleavage products. These data illustrate that the $TiO_2$/SWCNT composite catalyzes rapid phenol loss, slower ring cleavage, and limited reactivity with aliphatic products. The phenol decay results (FIG. 3) illustrate that pure phase anatase alone is less reactive than P25, and the negligible TOC and oxalic acid loss (FIG. 4) indicate that its reactivity is selective. In comparison to anatase and P25, the coupling of anatase nanoparticles into a SWCNT composite creates a more active photocatalyst for targeted reactions (e.g., phenol), but at the same time it retains some of the selectivity of the pure anatase (e.g. limited TOC and oxalic acid decay). These properties are useful for reducing the toxicity of chemical mixtures, but allow for chemical recovery in sustainable, closed-loop modes of operation.

4. Enhanced Photocatalysis

Figure 5:
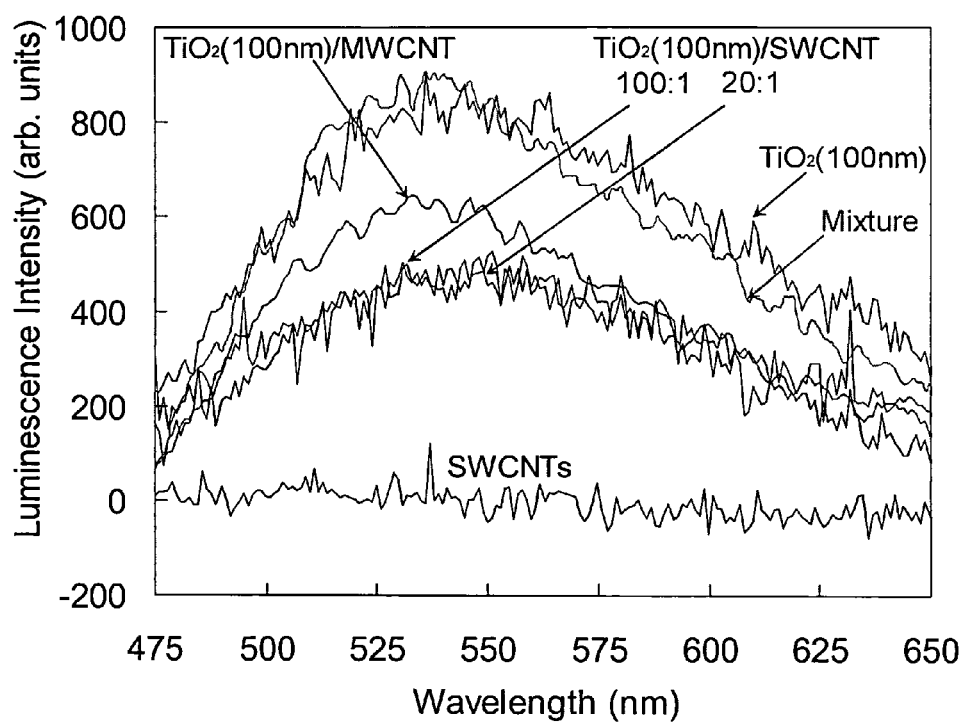
FIG. 5 shows photoluminescence spectra of $TiO_2$ (100 nm), $TiO_2$ (100 nm)/MWCNT, $TiO_2$ (100 nm)/SWCNT, SWCNTs and mixture of $TiO_2$ (100 nm) and SWCNTs.

Photocatalytic activity is, in part, a function of the lifetime and trapping of electrons and holes. Photoluminescence (PL) is often employed to study surface structure and excited states and to follow surface processes involving electron/hole fate $TiO_2$ (16, 31, 32). With electron-hole pair recombination after a photocatalyst is irradiated (e.g., via laser), photons are emitted, resulting in photoluminescence. This behavior is attributed to the reverse radiative deactivation from the excited state of the Ti species. The PL spectra shown in FIG. 5 compare the electron-hole recombination of various composites to anatase and the SWCNTs alone. The PL spectrum for the 100 nm anatase material is characterized by a broad peak at around 540 nm (31). Small differences in the maximum PL intensity may occur for different powders due to $TiO_x$ defects in the $TiO_2$ powders. Peak shifts are caused by the trapping of electrons at defect sites prior to recombination (31). No luminescence was observed in the range of 500 to 700 nm for the SWCNTs. The $TiO_2$/CNT samples showed diminished PL intensity indicating reduced charge recombination in comparison to anatase alone. This reduction is greater in the SWCNT composites than the MWCNT composite, which is consistent with evidence of better attachment for the $TiO_2$/SWCNT composite than the $TiO_2$/MWCNT composite (FIG. 2). A mixture of $TiO_2$ (100 nm) and SWCNTs (without going through the hydration/dehydration process) was also tested, and no PL intensity reduction was observed indicating again that the hydration/dehydration process is important for recombination reduction.

Figure 6:
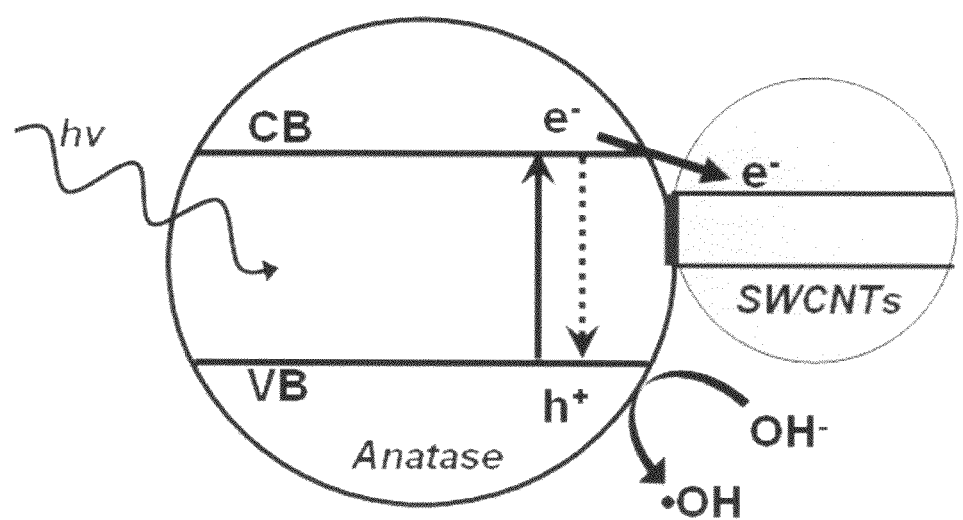
FIG. 6 shows a schematic of a proposed model for SWCNT-enhanced photocatalysis of anatase.

While the present invention is not limited to any particular mechanism, and an understanding of the mechanism is not necessary to practice the present invention, a proposed mechanism for the enhanced photocatalysis of the $TiO_2$/SWCNT composite is shown schematically in FIG. 6. An anatase nanoparticle is in intimate contact with SWCNTs, illustrated by the thickened line at the solid-solid interface of the two materials. Under UV illumination, electrons ($e^-$) are excited from the valence band (VB) to the conduction band (CB) of the anatase, creating a charge vacancy, or hole ($h^+$), in the VB. In the absence of the SWCNTs, most of these charges quickly recombine without doing any chemistry. Typically, only a small number of electrons (<1%) and holes are trapped and participate in photocatalytic reactions, resulting in low reactivity (1, 6). It has been reported that the CB position of anatase is about −4.21 eV using vacuum level (AVS) as a reference, with a bandgap of about 3.2 eV (33). And the work function of SWCNTs is known to be around −4.8 eV (AVS) with a narrow bandgap ranging from 0 to 1.1 eV (34). When SWCNTs are attached to the surface of the anatase, the relative position of the SWCNT conduction band edge permits the transfer of electrons from the anatase surface, allowing charge separation, stabilization, and hindered recombination. The electrons can be shuttled freely along the conducting network of the SWCNT bundle. The longer-lived holes on the anatase, then, account for the higher activity of the composite photocatalyst. The anatase/MWCNT composites behave similarly, but as illustrated in FIG. 3 do not enhance the photocatalytic activity of anatase to the same extent as the SWCNT because there is much less individual contact between the MWCNT and the anatase surface.

SUMMARY

This example has demonstrated that a simple hydration/dehydration method effectively creates $TiO_2$/CNT composites that enhance the photocatalytic reactivity, while retaining some of the selectivity of anatase. The hydration/dehydration processing is an important part of fabricating active composites. In contrast to previous reports, there was no observation of a positive photocatalytic effect from simply mixing CNTs with $TiO_2$ presumably due to light attenuation by the CNTs. The present Example examined whether there is a particular $TiO_2$/CNT arrangement that optimizes their interaction to produce high reactive surface area (disperse catalyst), hindered charge recombination, and enhanced photocatalytic oxidation. By tuning the relative sizes and mass ratios of the $TiO_2$ and CNTs, and using a simple hydration/dehydration procedure to produce $TiO_2$/CNT composites, this methods optimizes the interphase contact between the $TiO_2$ and CNTs. While all of the composites showed reduced charge recombination as measured by photoluminescence spectra, a 20:1 mass ratio between 100 nm anatase particles and SWCNTs produced a composite having a structure consistent with the conceptual picture shown in FIG. 1(c) and the highest reactivity as measured by phenol degradation. The particular advantage of SWCNTs over MWCNTs is associated with the greater degree of interphase contact that can be achieved at the $TiO_2$ surface with the bundle of small individual SWCNTs, as shown in FIGS. 1(c) and 2(f). This structure also provides better dispersion and support of the anatase, thereby enhancing the reactive surface area of the catalyst (36). The anatase/SWCNT composites are useful for various environmental applications, including water and air purification as well as chemical recovery processes. They may also be applied in dye-sensitized solar cells to enhance the electron transfer in the $TiO_2$ electrodes (34, 35, 37). Their preparation, as demonstrated in this Example, only involves a hydration/dehydration process, which is much simpler than the sol-gel, CVD, or PVD methods and suitable for large-scale production.

Example 2

Photocatalytic Methods with $TiO_2$/SWCNT Composites

Figure 7:
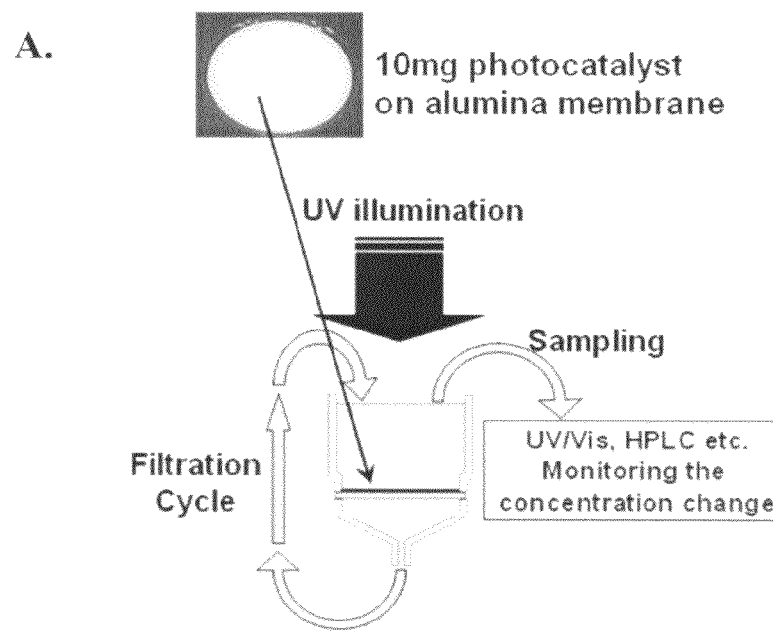
Figure 7:
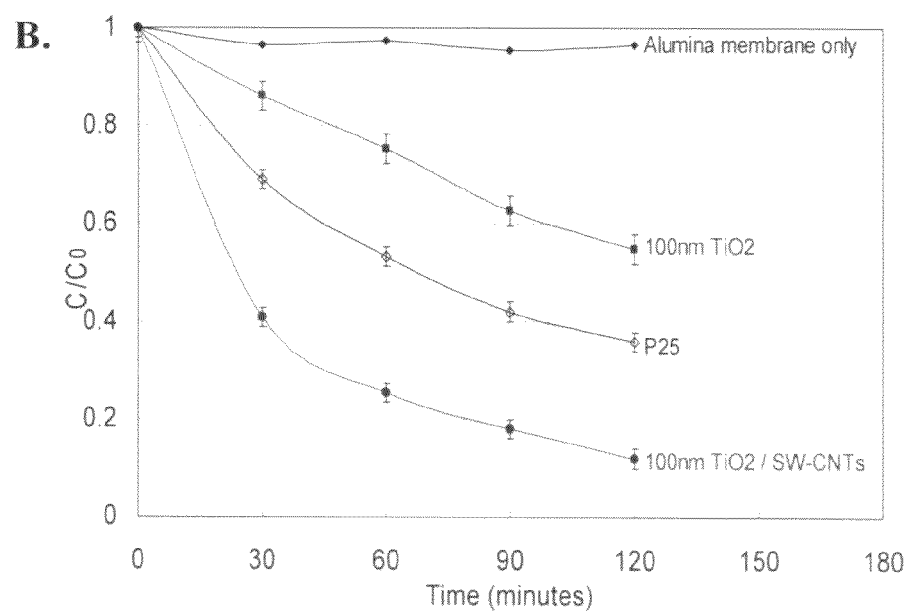

The $TiO_2$/SWCNTs of the present invention many be used for many different photocatalytic applications. For example, such composites find utility in methods for purifying water contaminated by organic pollutants. To demonstrate this application, a layer of L-anatase/SWCNT composite was added to an alumina ceramic disk membrane filter (although any other suitable type of filter may be employed) the treated surface was exposed to UV light while recirculating a phenol solution through the filter, as shown in FIG. 7. Much like the suspension tests, the L-anatase/SWCNT shows a remarkable reduction in the phenol concentration compared to the untreated alumina disk membrane, a membrane treated only with the L-anatases (100 mm $TiO_2$), and the photocatalytic standard of P25 (FIG. 7B). Thus, in one embodiment this photocatalytic composite filters water contaminated with organic compounds, such as phenol or other compounds.

Other organic compounds are also oxidized by the L-anatase/SWCNT photocatalyst. In other embodiments, the photocatalyst is useful in the prevention of biofouling. Since the L-anatase/SWCNT attacks organic compounds, it damages or inactivates the bacteria that cause biofouling. In further embodiments, the L-anatase/SWCNTs composites are utilized for various environmental applications, including but not limited to, methods for water remediation and air purification. The composites may also be used in applications for dye-sensitized solar cells to enhance the electron transfer in the $TiO_2$ electrodes. Additional applications for compositions of the present invention are described in the following patents and patent applications, each of which is herein incorporated by reference in its entirety: U.S. Pat. No. 4,806,514, U.S. Pat. No. 5,541,096, U.S. Pat. No. 6,048,499, U.S. Pat. No. 6,306,296, U.S. Pat. No. 6,372,095, U.S. Pat. No. 6,464,951, U.S. Pat. No. 6,924,140, U.S. Pat. No. 7,022,241, US2003/0000824A1, US2003/0189930A1, US2004/0040831A1, US2004/0182792A1 and WO06/107308.

Example 3

$ZrO_2$ Ceramic Membranes Coated with $TiO_2$/SWNCT Composite

This Example describes generating $ZrO_2$ ceramic membranes coated with $TiO_2$/SWNCT composite material. Such membranes may be used for many purposes, such as those involving photoreactivity.

$TiO_2$-based photocatalysts have been extensively studied for environmental applications including water and air purification, self-cleaning surfaces, water photo-splitting, and photovoltaics (1-5-A). A uniform layer of $TiO_2$ with large effective surface area and high reactivity is critical for many $TiO_2$-related applications. For example, in a typical commercial photocatalytic air purifier, a porous ceramic filter coated with particulate $TiO_2$ is often used to remove odors and kill bacteria under UV illumination (2-A, herein incorporated by reference). In another case, deposition of $TiO_2$ on an inert support is applied for water purification (1-A, herein incorporated by reference). Deposition methods for $TiO_2$ include chemical vapor deposition (CVD) (6-A), physical vapor deposition (PVD) (7-A), sol-gel dip-coating plus sintering (3-5-A, 8-A, 9-A), the doctor-blade technique (4-A, 5-A), and dip-coating using a particulate suspension and sintering (1-A). Among these, dip-coating, which is described below, requires minimal facilities and expertise and therefore holds significant potential for large scale production.

The reactivity of the $TiO_2$ layer is an important factor. Extensive effort has been directed toward enhancing $TiO_2$ reactivity. For example, by using mixed-phase $TiO_2$, much higher reactivity can be obtained than with pure-phase $TiO_2$ (10-12-A). Likewise, the reactivity of anatase phase $TiO_2$ particles can be enhanced by combining them with single-walled carbon nanotubes (SWCNTs) through a simple hydration-dehydration process as described in Example 1 above (see also, 13-A, 14-A, both of which are herein incorporated by reference). As described in Example 1, the resulting anatase/SWCNT composite has much higher reactivity than the traditional "gold standard", Degussa P25, for the photo-degradation of phenol in a slurry. Not only do SWCNTs enhance the reactivity of $TiO_2$, but they also facilitate the uniform dispersion of $TiO_2$ particles and thereby improve the quality of the $TiO_2$ coating on porous zirconia supports.

In this Example, three types of materials were dip-coated on ceramic supports: anatase particles, anatase/SWCNT composites, and anatase/MWCNT (multi-walled carbon nanotube) composites. The anatase phase $TiO_2$ powder (Analytical Grade purchased from Sigma-Aldrich, product #232033) has an average particle size of 100 nm according to the manufacturer. Based on our SEM characterization, the particle diameters range from 40 nm to 300 nm, with an average of ~130 nm and standard deviation of ~70 nm. The BET surface area is 8.6 $m^2/g$, and X-Ray diffraction confirms that the $TiO_2$ is pure anatase phase.

SWCNTs (Carbon Solutions, Inc.) synthesized by an electric arc discharge method were treated in a reflux system with concentrated nitric acid (70%) at ~150° C. for 1 hour to remove the Ni/Y catalyst and amorphous carbon impurities. Likewise, MWCNTs (NanoTech Labs Inc.) prepared using chemical vapor deposition were also treated in a nitric acid reflux system. In general, acid treatment of CNTs tends to functionalize the nanotube walls with carboxyl groups, which may enhance the adsorption of $TiO_2$ or organic compounds on the CNTs (15-A, 16-A). Based on SEM characterization, the SWCNTs tend to occur as bundles with average bundle diameters of 2-10 nm. According to the manufacturer, the bundles are 1-5 μm long, and the individual tubes are 0.5-3.0 μm long with an average diameter of 1.4 nm. The MWCNTs have a diameter of 20-30 nm based on our SEM characterization and a length of ~30 μm according to the manufacturer.

The anatase/SWCNT composite material was prepared via a simple hydration-dehydration process, in which a water suspension containing the anatase $TiO_2$ and SWCNTs was evaporated on a 80° C. hot plate and dried in 104° C. oven, as described in Example 1 (see, 14-A). The mass ratio between the $TiO_2$ and SWCNTs was 100:1 to minimize the use of expensive SWCNTs. The anatase/MWCNT composite material was prepared using the same hydration-dehydration method.

$TiO_2$ was deposited on ceramic discs (47 mm diameter, 2.5 mm thick, Sterlitech Corporation, product #47U300) by dip-coating and sintering. These ceramic discs are sold as ultrafiltration membranes with a porous zirconia top layer and a molecular weight cut-off of 300 kiloDalton (~15 nm pores). The coated top surface of the discs has a root mean square roughness of 98 nm prior to depositing the $TiO_2$, with a standard deviation of 19 nm based on JEOL scanning probe microscope measurements (JSPM-5200). The dry $TiO_2$ or $TiO_2$/CNT composite was added to a water suspension in a concentration of 1 g/L and sonicated for 1 minute. The pH value of the suspension was 5 for the pure anatase and both anatase/CNT composites. Dip-coating was conducted at pH values of 3, 5, and 8 by adding hydrochloric acid (0.01M) or sodium hydroxide (0.01M) to adjust the pH of the suspension. To apply the $TiO_2$, the ceramic discs were rinsed with acetone and MilliQ water and then dried in a 104° C. oven for at least 2 hours. The disc was removed from the oven and immediately submerged into the $TiO_2$ suspension for 5 seconds while it was still warm. After slowly removing from the suspension, the disc was placed back into the 104° C. oven for 2 hours to evaporate the water, with the target surface (porous zirconia surface) facing up. The disc was then gradually heated up to 250° C. with a ramp rate of 5° C./minute. After heat treatment at 250° C. for one hour, the oven was turned off and gradually cooled to around 104° C. The dipping and sintering process was repeated four times for each disc. Discs were also prepared using a typical surfactant, Triton X-100, to consider the effect of a surfactant on the dispersion of $TiO_2$ on the surface. The dry $TiO_2$ was added to a 0.5% Triton X-100 aqueous solution, and the same dip-coating process was conducted.

Figure 8:
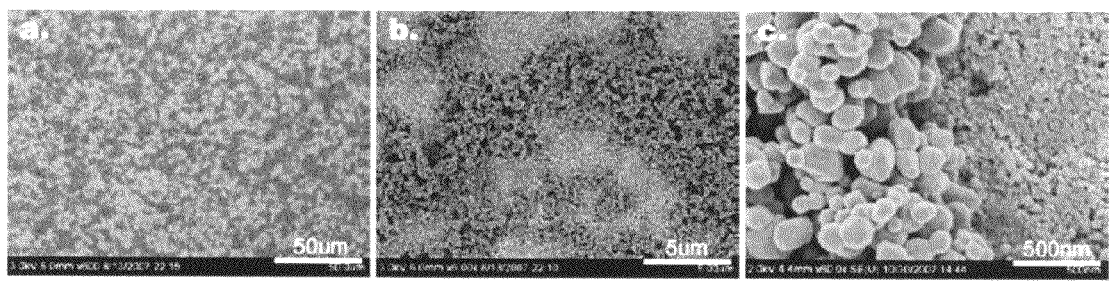
FIG. 8 shows SEM images of ceramic surfaces after dip-coating with $TiO_2$ at pH 5.

After the dip-coating, the surface coating on the discs was observed using a scanning electron microscope (SEM, Hitachi S4800). FIG. 8 shows the SEM images of the ceramic disc surface after the deposition of pure anatase $TiO_2$ at pH 5 for three levels of magnification. In the low magnification image, the dark areas are $TiO_2$ particles, and the light areas are bare ceramic membrane surface. From the high magnification images, the $TiO_2$ nano-particles tend to aggregate and clump on the surface of the zirconia ceramic membrane support. No improvement in coverage was observed when the surfactant Triton X-100 was used.

The $TiO_2$ coating at pH 5 is more uniform than similar coatings at pH 3 and 8. At pH 3 there are widely separated clumps of $TiO_2$ with no coverage in between, and at pH 8 there are thin stripes of $TiO_2$, though clumping is reduced. In addition, the degree of coverage is better at pH 5 than either pH 3 or pH 8. To quantify this effect, image processing software (Image J) was used to calculate the coverage at several different locations on the surface. The dark and light areas were separated using the "threshold" function, and then the area fraction was calculated using the "measurement" function. The average coverage of the ceramic surface by the $TiO_2$ coating was ~28% at pH 3, ~45% at pH 5, and ~18% at pH 8.

Figure 9:
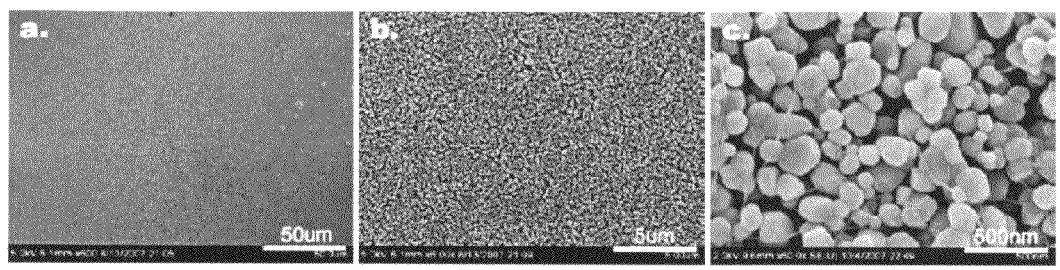
FIG. 9 shows SEM images of ceramic surfaces after dip-coating with $TiO_2$/SWCNT at pH 5.

The situation is quite different after the deposition of $TiO_2$/SWCNT composite at pH 5, as shown in FIG. 9. From the low magnification image, it is evident that the anatase/SWCNT coating is highly uniform and complete. The coating reaches 100% coverage and does not display any cracking, a problem that occurs with sol-gel coatings (9-A). The higher magnification images show the structure of the anatase/SWCNT composite coatings. The SWCNT bundles, which have diameters of around 10 nm, are well dispersed and interwoven among the anatase particles. The SWCNT bundles also appear to closely attach to the $TiO_2$ particle surfaces. Similar attachment between the SWCNT bundles and the anatase particles was found to be an important factor in the synergistic effect between the nanotubes and $TiO_2$ that leads to high photo-reactivity (14-A). At pH 5, SWCNTs are negatively charged (17-A) and $TiO_2$ is positively charged (18-A). While the present invention is not limited to any mechanism, and an understanding of the mechanism is not necessary to practice the present invention, it would appear that the opposite charges leads to more favorable conditions for dispersion of the $TiO_2$ particles with SWCNTs than for the clumping of $TiO_2$ particles due to their like charge. At pH 3 and 8, the uniformity and coverage of anatase/SWCNT coating is also better than that for pure $TiO_2$, but not as good as at pH 5. It appears that the chemical bonding due to the hydration-dehydration step partially overcomes the electrostatic effects that should prohibit interaction between $TiO_2$ and SWCNTs so reasonably good dispersion occurs anyway.

Figure 10:
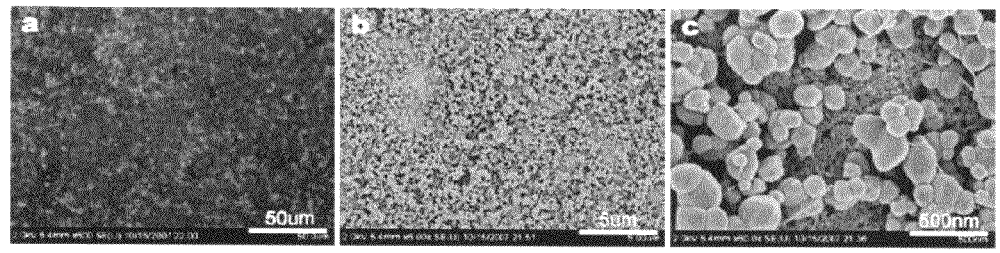
FIG. 10 shows SEM images of ceramic surfaces after dip-coating with $TiO_2$+SWCNT mixture (added to a suspension separately without hydration-dehydration) at pH 5.

To evaluate the necessity of creating a composite of $TiO_2$ particles and SWCNTs before coating the zirconia, a control test was conducted using a simple suspension of anatase $TiO_2$ particles and SWCNTs (denoted as $TiO_2$+SWCNT) without using the hydration-dehydration process to form a composite. The zirconia ceramic discs were dip-coated in a suspension of this simple mixture following the same procedures at a pH of 5. As shown in FIG. 10, at low magnification the uniformity and degree of coverage are better than pure anatase $TiO_2$ (FIG. 1), indicating that the simple addition of SWCNTs in the $TiO_2$ suspension improves the $TiO_2$ coating on the ceramic surfaces. However, the coverage using the mixture is less extensive compared to the anatase/SWCNT composite (FIG. 9), because the hydration-dehydration creates better connection between $TiO_2$ particles and SWCNT bundles (13-A, 14-A), resulting in more uniform dispersion of the $TiO_2$ particles.

Figure 11:
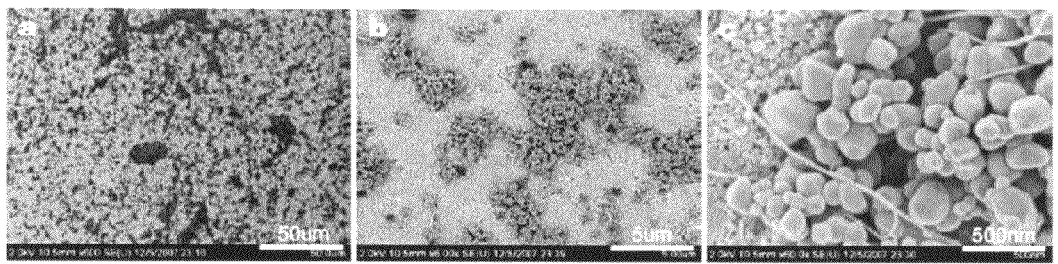
FIG. 11 shows SEM images of ceramic surfaces after dip-coating with $TiO_2$/MWCNT at pH 5.

The uniformity and coverage for the anatase/MWCNT composite at pH 5, as shown in FIG. 11, was less than those observed for anatase/SWCNT composite (FIG. 9). As illustrated in FIG. 11c, the $TiO_2$ particles are not well dispersed because of the relatively poor contact between $TiO_2$ particles and stiff MWCNTs.

Figure 12:
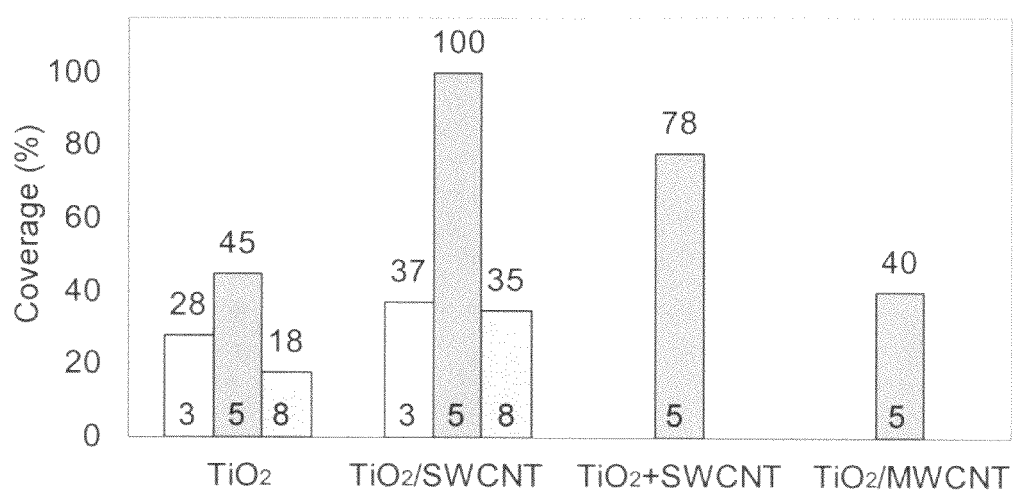
FIG. 12 shows coverage of ceramic surface by $TiO_2$, $TiO_2$/CNT composites, and $TiO_2$+SWCNT mixture, at pH 3, 5 and 8.

FIG. 12 compares the coverage for all the materials tested. The general improvement in coverage at pH 5 is related to the surface charges of both the $TiO_2$ particles and the $ZrO_2$ surface. The zero point charge is pH 4.18 for $ZrO_2$ (19-A) and pH 6.85 for $TiO_2$ (18-A). Therefore, at pH 5, favorable electrostatic interactions exist between the negatively charged surface of the zirconia membrane and the positively charged surface of the $TiO_2$ particles, accounting for the better overall coverage at this pH. In contrast, at either pH 3 ($TiO_2$ and $ZrO_2$ surfaces are both positively charged) or pH 8 (both surfaces are negatively charged), unfavorable electrostatic interactions prevail, explaining the clumping and reduced coverage. The chemical bonding between SWCNT and $TiO_2$ produced by the hydration-dehydration processing is more energetically favorable than electrostatic interactions and results in a well dispersed (reduced clumping) catalyst (14-A). This dispersive effect of SWCNTs in combination with the favorable electrostatic interactions between $TiO_2$ and $ZrO_2$ at pH 5 results in a highly uniform coating of the $TiO_2$/SWCNT composite.

In summary, the above Examples shows successful preparation of uniform $TiO_2$ coatings on $ZrO_2$ membranes by using a $TiO_2$/SWCNT composite, which has also shown improved photocatalytic activity as described in Example 1. Dip-coating is an easy and economical way to coat $TiO_2$ particles on various surfaces. Incorporating SWCNTs improves both the uniformity and coverage of $TiO_2$ particles on zirconia membrane discs.

REFERENCES (1) Bickley, R. I.; Gonzalezcarreno, T.; Lees, J. S.; Palmisano, L.; Tilley, R. J. D. A Structural Investigation of Titanium-Dioxide Photocatalysts. Journal of Solid State Chemistry 1991, 92, 178-190.
(2) Hurum, D. C.; Agrios, A. G.; Crist, S. E.; Gray, K. A.; Rajh, T.; Thurnauer, M. C. Probing reaction mechanisms in mixed phase $TiO_2$ by EPR. Journal of Electron Spectroscopy and Related Phenomena 2006, 150, 155-163.
(3) Hurum, D. C.; Agrios, A. G.; Gray, K. A.; Rajh, T.; Thurnauer, M. C. Explaining the enhanced photocatalytic activity of Degussa P25 mixed-phase $TiO_2$ using EPR. Journal of Physical Chemistry B 2003, 107, 4545-4549.
(4) Hurum, D. C.; Gray, K. A.; Rajh, T.; Thurnauer, M. C. Recombination pathways in the Degussa P25 formulation of $TiO_2$: Surface versus lattice mechanisms. Journal of Physical Chemistry B 2005, 109, 977-980.
(5) Kamat, P. V. Photoinduced transformations in semiconductor-metal nanocomposite assemblies. Pure and Applied Chemistry 2002, 74, 1693-1706.
(6) Li, G.; Gray, K. A. The Solid-Solid Interface: Explaining the High and Unique Photocatalytic Reactivity of $TiO_2$-Based Nanocomposite Materials. Chemical Physics 2007, 339, 173-187.
(7) Rajeshwar, K.; de Tacconi, N. R.; Chenthamarakshan, C. R. Semiconductor-based composite materials: Preparation, properties, and performance. Chemistry of Materials 2001, 13, 2765-2782.
(8) Chen, Y.; Dionysiou, D. D. A comparative study on physicochemical properties and photocatalytic behavior of macroporous $TiO_2$-P25 composite films and macroporous $TiO_2$ films coated on stainless steel substrate. Applied Catalysis, A: General 2007, 317, 129-137.

(9) Yoo, K. S.; Choi, H.; Dionysiou, D. D. Synthesis of anatase nanostructured $TiO_2$ particles at low temperature using ionic liquid for photocatalysis. Catalysis Communications 2005, 6, 259-262.

(10) Chen, Y.; Crittenden, J. C.; Hackney, S.; Sutter, L.; Hand, D. W. Preparation of a Novel $TiO_2$-Based p-n Junction Nanotube Photocatalyst. Environmental Science and Technology 2005, 39, 1201-1208.

(11) Zhang, Y.; Crittenden, J. C.; Hand, D. W.; Perram, D. L. Fixed-bed photocatalysts for solar decontamination of water. Environmental Science and Technology 1994, 28, 435-42.

(12) Arana, J.; Dona-Rodriguez, J. M.; Tello Rendon, E.; Garriga i Cabo, C.; Gonzalez-Diaz, O.; Herrera-Melian, J. A.; Perez-Pena, J.; Colon, G.; Navio, J. A. $TiO_2$ activation by using activated carbon as a support. Part I. Surface characterization and decantability study. Applied Catalysis, B: Environmental 2003, 44, 161-172.

(13) Arana, J.; Dona-Rodriguez, J. M.; Tello Rendon, E.; Garriga i Cabo, C.; Gonzalez-Diaz, O.; Herrera-Melian, J. A.; Perez-Pena, J.; Colon, G.; Navio, J. A. $TiO_2$ activation by using activated carbon as a support. Part II. Photoreactivity and FTIR study. Applied Catalysis, B: Environmental 2003, 44, 153-160.

(14) Wang, W.; Serp, P.; Kalck, P.; Faria, J. L. Photocatalytic degradation of phenol on MWNT and titania composite catalysts prepared by a modified sol-gel method. Applied Catalysis, B: Environmental 2005, 56, 305-312.

(15) Lee, S.-H.; Pumprueg, S.; Moudgil, B.; Sigmund, W. Inactivation of bacterial endospores by photocatalytic nanocomposites. Colloids and Surfaces, B: Biointerfaces 2005, 40, 93-98.

(16) Yu, Y.; Yu, J. C.; Chan, C.-Y.; Che, Y.-K.; Zhao, J.-C.; Ding, L.; Ge, W.-K.; Wong, P.-K. Enhancement of adsorption and photocatalytic activity of $TiO_2$ by using carbon nanotubes for the treatment of azo dye. Applied Catalysis, B: Environmental 2005, 61, 1-11.

(17) Feng, W.; Feng, Y.; Wu, Z.; Fujii, A.; Ozaki, M.; Yoshino, K. Optical and electrical characterizations of nanocomposite film of titania adsorbed onto oxidized multiwalled carbon nanotubes. Journal of Physics: Condensed Matter 2005, 17, 4361-4368.

(18) Kang, S.-Z.; Cui, Z.; Mu, J. Composite of carboxyl-modified multi-walled carbon nanotubes and $TiO_2$ nanoparticles: preparation and photocatalytic activity. Fullerenes, Nanotubes, and Carbon Nanostructures 2007, 15, 81-88.

(19) Fan, W.; Gao, L.; Sun, J. Anatase $TiO_2$-coated multi-wall carbon nanotubes with the vapor phase method. Journal of the American Ceramic Society 2006, 89, 731-733.

(20) Jitianu, A.; Cacciaguerra, T.; Benoit, R.; Delpeux, S.; Beguin, F.; Bonnamy, S. Synthesis and characterization of carbon nanotubes-$TiO_2$ nanocomposites. Carbon 2004, 42, 1147-1151.

(21) Yu, H.; Zhao, H.; Quan, X.; Chen, S. Preparation and characterization of aligned carbon nanotubes coated with titania nanoparticles. Chinese Science Bulletin 2006, 51, 2294-2296.

(22) Thostenson, E. T.; Ren, Z.; Chou, T.-W. Advances in the science and technology of carbon nanotubes and their composites: a review. Composites Science and Technology 2001, 61, 1899-1912.

(23) Agrios, A. G.; Gray, K. A.; Weitz, E. Photocatalytic transformation of 2,4,5-trichlorophenol on $TiO_2$ under sub-band-gap illumination. Langmuir 2003, 19, 1402-1409.

(24) Andrade, L. S.; Laurindo, E. A.; de Oliveira, R. V.; Rocha-Filho, R. C.; Cass, Q. B. Development of a HPLC method to follow the degradation of phenol by electrochemical or photoelectrochemical treatment. Journal of the Brazilian Chemical Society 2006, 17, 369-373.

(25) Guidelines for Use and Care of Aminex Resin-Based Columns, Bio-Rad Laboratories, LIT-42 Rev B.

(26) APHA Standard Method 5310 B. High Temperature Combustion Method. APHA, 1998. Standard Methods for the Examination of Water and Wastewater. American Public Health Association, Washington. 20th edition, 5.20-5.22.

(27) Kis, A.; Csanyi, G.; Salvetat, J.-P.; Lee, T.-N.; Couteau, E.; Kulik, A. J.; Benoit, W.; Brugger, J.; Forro, L. Reinforcement of single-walled carbon nanotube bundles by intertube bridging. Nature Materials 2004, 3, 153-157.

(28) Salvetat, J.-P.; Kulik, A. J.; Bonard, J.-M.; Briggs, G. A. D.; Stoeckli, T.; Metenier, K.; Bonnamy, S.; Beguin, F.; Burnham, N. A.; Forro, L. Elastic modulus of ordered and disordered multiwalled carbon nanotubes. Advanced Materials 1999, 11, 161-165.

(29) Elser, M. J.; Berger, T.; Brandhuber, D.; Bernardi, J.; Diwald, O.; Knoezinger, E. Particles Coming Together: Electron Centers in Adjoined $TiO_2$ Nanocrystals. Journal of Physical Chemistry B 2006, 110, 7605-7608.

(30) Zhang, Z.; Wang, C.-C.; Zakaria, R.; Ying, J. Y. Role of Particle Size in Nanocrystalline $TiO_2$-Based Photocatalysts. Journal of Physical Chemistry B 1998, 102, 10871-10878.

(31) Fujihara, K.; Izumi, S.; Ohno, T.; Matsumura, M. Time-resolved photoluminescence of particulate $TiO_2$ photocatalysts suspended in aqueous solutions. Journal of Photochemistry and Photobiology, A: Chemistry 2000, 132, 99-104.

(32) Anpo, M.; Tomonari, M.; Fox, M. A. In situ photoluminescence of titania as a probe of photocatalytic reactions. Journal of Physical Chemistry B 1989, 93, 7300-2.

(33) Xu, Y.; Schoonen, M. A. A. The absolute energy positions of conduction and valence bands of selected semiconducting minerals. American Mineralogist 2000, 85, 543-556.

(34) Robel, I.; Bunker, B. A.; Kamat, P. V. Single-walled carbon nanotube-CdS nanocomposites as light-harvesting assemblies: Photoinduced charge-transfer interactions. Advanced Materials (Weinheim, Germany) 2005, 17, 2458-2463.

(35) Kim, S. L.; Jang, S.-R.; Vittal, R.; Lee, J.; Kim, K.-J. Rutile $TiO_2$-modified multi-wall carbon nanotubes in $TiO_2$ film electrodes for dye-sensitized solar cells. Journal of Applied Electrochemistry 2006, 36, 1433-1439.

(36) Kongkanand, A.; Martinez Dominguez, R.; Kamat, P. V. Single Wall Carbon Nanotube Scaffolds for Photoelectrochemical Solar Cells. Capture and Transport of Photogenerated Electrons. Nano Letters 2007, 7, 676-680.

(37) Jang, S.-R.; Vittal, R.; Kim, K.-J. Incorporation of Functionalized Single-Wall Carbon Nanotubes in Dye-Sensitized $TiO_2$ Solar Cells. Langmuir 2004, 20, 9807-9810.

(1-A) Bideau, M.; Claudel, B.; Dubien, C.; Faure, L.; Kazouan, H. On the "immobilization" of titanium dioxide in the photocatalytic oxidation of spent waters. Journal of Photochemistry and Photobiology A: Chemistry 1995, 91, 137-144.

(2-A) Fujishima, A.; Zhang, X. Titanium dioxide photocatalysis: present situation and future approaches. Comptes Rendus: Chimie 2006, 9, 750-760.

(3-A) Wang, R.; Hashimoto, K.; Fujishima, A.; Chikuni, M.; Kojima, E.; Kitamura, A.; Shimohigoshi, M.; Watanabe, T.

Photogeneration of Highly Amphiphilic TiO$_2$ Surfaces. Advanced Materials 1998, 10, 135-138.

(4-A) Burnside, S. D.; Shklover, V.; Barbe, C.; Pascal Comte; Arendse, F.; Brooks, K.; Gratzel, M. Self-Organization of TiO$_2$ Nanoparticles in Thin Films. Chem. Mater. 1998, 10, 2419-2425.

(5-A) Zhang, D.; Downing, J. A.; Knorr, F. J.; McHale, J. L. Room-Temperature Preparation of Nanocrystalline TiO$_2$ Films and the Influence of Surface Properties on Dye-Sensitized Solar Energy Conversion. J. Phys. Chem. B 2006, 110, 21890-21898.

(6-A) Boyd, D. A.; Greengard, L.; Brongersma, M.; El-Naggar, M. Y.; Goodwin, D. G. Plasmon-Assisted Chemical Vapor Deposition. NANO LETTERS 2006, 6, 2592-2597.

(7-A) Chen, L.; Graham, M. E.; Li, G.; Gray, K. A. Fabricating Highly Active Mixed-Phase TiO$_2$ Photocatalysts by Reactive DC Magnetron Sputter Deposition. Thin Solid Films 2006, 515, 1176-1181.

(8-A) Guo, B.; Liu, Z.; Hong, L.; Jiang, H. Sol gel derived photocatalytic porous TiO$_2$ thin films. Surface & Coatings Technology 2005, 198, 24-29.

(9-A) Li, G.; Ciston, S.; Saponjic, Z. V.; Chen, L.; Dimitrijevic, N. M.; Rajh, T.; Gray, K. A. Synthesizing mixed-phase TiO$_2$ nanocomposites using a hydrothermal method for photo-oxidation and photoreduction applications. Journal of Catalysis 2008, 253, 105-110.

(10-A) Hurum, D. C.; Agrios, A. G.; Crist, S. E.; Gray, K. A.; Rajh, T.; Thurnauer, M. C. Probing reaction mechanisms in mixed phase TiO$_2$ by EPR. Journal of Electron Spectroscopy and Related Phenomena 2006, 150, 155-163.

(11-A) Li, G.; Gray, K. A. The Solid-Solid Interface: Explaining the High and Unique Photocatalytic Reactivity of TiO$_2$-Based Nanocomposite Materials. Chemical Physics 2007, 339, 173-187

(12-A) Hurum, D. C.; Agrios, A. G.; Gray, K. A.; Rajh, T.; Thurnauer, M. C. Explaining the enhanced photocatalytic activity of Degussa P25 mixed-phase TiO$_2$ using EPR. Journal of Physical Chemistry B 2003, 107, 4545-4549.

(13-A) Elser, M. J.; Berger, T.; Brandhuber, D.; Bernardi, J.; Diwald, O.; Knoezinger, E. Particles Coming Together: Electron Centers in Adjoined Ti$_{O2}$ Nanocrystals. Journal of Physical Chemistry B 2006, 110, 7605-7608.

(14-A) Yao, Y.; Li, G.; Ciston, S.; Lueptow, R. M.; Gray, K. A. Photoreactive TiO$_2$/Carbon Nanotube Composites: Synthesis and Reactivity. Environmental Science & Technology, accepted.

(15-A) Thostenson, E. T.; Ren, Z.; Chou, T.-W. Advances in the science and technology of carbon nanotubes and their composites: a review. Composites Science and Technology 2001, 61, 1899-1912.

(16-A) Wang, W.; Serp, P.; Kalck, P.; Faria, J. L. Photocatalytic degradation of phenol on MWNT and titania composite catalysts prepared by a modified sol-gel method. Applied Catalysis, B: Environmental 2005, 56, 305-312.

(17-A) Poyato, R.; Vasiliev, A. L.; Padture, N. P.; Tanaka, H.; Nishimura, T. Aqueous colloidal processing of single-wall carbon nanotubes and their composites with ceramics. Nanotechnology 2006, 17, 1770-1777.

(18-A) Ridley, M. K.; Hackley, V. A.; Machesky, M. L. Characterization and Surface-Reactivity of Nanocrystalline Anatase in Aqueous Solutions. Langmuir 2006, 22, 10972-10982.

(19-A) Klimova, T.; Rojas, M. L.; Castillo, P.; Cuevas, R.; Ramirez, J. Characterization of Al2O3-ZrO$_2$ mixed oxide catalytic supports prepared by the sol-gel method. Microporous and Mesoporous Materials 1998, 20, 293-306.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition comprising: a composite material comprising TiO$_2$ particles and single-walled carbon nanotubes (SWCNTs), wherein said SWCNTs decorate, bridge between, and are interwoven among said TiO$_2$ particles in said composite material, and wherein said TiO$_2$ particles have an average diameter between 120 and 140 nm.

2. The composition of claim 1, wherein the ratio of said TiO$_2$ particles to said SWCNTs is between 8:1 to 125:1.

3. The composition of claim 1, wherein said SWCNTs are about 1.0-2.0 nm in diameter.

4. The composition of claim 1, wherein said composite material is chemically reactive.

5. The composition of claim 1, wherein said SWCNTs are about 0.3 to about 4.0 microns in length.

6. The composition of claim 1, further comprising a base material upon which the composition is deposited.

7. The composition of claim 6, wherein said base material comprises ceramic material.

8. A method of making a chemically reactive TiO$_2$/SWCNT composite comprising:
   a) dispersing single-walled carbon nanotubes (SWCNTs) in water to generate a suspension;
   b) mixing TiO$_2$ particles into said suspension, wherein said TiO$_7$ particles have an average diameter between 120 and 140 nm;
   c) treating said suspension under conditions such that a dehydrated suspension is generated; and
   d) drying said dehydrated suspension under conditions such that a chemically reactive TiO$_2$/SWCNT composite is generated, wherein said SWCNTs decorate, bridge between, and are interwoven among said TiO$_2$ particles in said chemically reactive TiO$_2$/SWCNT composite.

9. The method of claim 8, wherein the ratio of said TiO$_2$ particles to said SWCNTs in said TiO$_2$/SWCNT composite is approximately 20:1.

10. The method of claim 8, wherein said treating step comprises removing water from suspension by evaporating.

11. The method of claim 8, wherein said drying step comprises maintaining said dehydrated suspension at an elevated temperature for at least 5 hours.

12. Method of treating a substrate comprising;
    a) providing a composite material comprising TiO$_2$ particles and single-walled carbon nanotubes (SWCNTs), wherein said SWCNTs decorate, bridge between, and are interwoven among said TiO$_2$ particles in said composite material, and wherein said TiO$_2$ particles have an average diameter between 120 and 140 nm;
    b) contacting said composite material with a substrate comprising organic contaminants; and
    c) activating said composite material under conditions such that at least a portion of said organic contaminants in said substrate are altered.

13. The method of claim 12, wherein said substrate comprises water or air.

14. The method of claim 12, wherein said organic contaminant are altered by being inactivated, destroyed, or converted into a non-contaminant.

15. The method of claim 12, further providing a membrane filter, wherein said composite material is located on and/or within said membrane filter.

16. The method of claim 12, wherein said activating comprises exposing said composite material to UV illumination.

17. Method of reducing fouling of an article comprising;
   a) providing an article subject to biological fouling, wherein said article comprises a composite material comprising $TiO_2$ particles and single-walled carbon nanotubes (SWCNTs), wherein said SWCNTs decorate, bridge between, and are interwoven among said $TiO_2$ particles in said composite material, and wherein said $TiO_2$ particles have an average diameter between 120 and 140 nm;
   b) contacting said article with a substrate comprising biological contaminants; and
   c) photoactivating said composite material under conditions such that at least a portion of said biological contaminants in said substrate are altered, thereby reducing or preventing fouling of said article.

18. The method of claim 17, wherein said article comprises a membrane.

19. The method of claim 17, wherein said biological contaminants comprise bacteria.

* * * * *

UNITED STATES PATENT AND TRADEMARK OFFICE
CERTIFICATE OF CORRECTION

PATENT NO. : 9,078,942 B2  
APPLICATION NO. : 12/152481  
DATED : July 14, 2015  
INVENTOR(S) : Yuan Yao et al.

Page 1 of 1

It is certified that error appears in the above-identified patent and that said Letters Patent is hereby corrected as shown below:

Claim 8, column 20, line 37 should read as follows
$TiO_2$ particles have an average diameter between 120

Signed and Sealed this
Twelfth Day of April, 2016

Michelle K. Lee
*Director of the United States Patent and Trademark Office*